United States Patent [19]
Kojima et al.

[11] Patent Number: 5,895,591
[45] Date of Patent: Apr. 20, 1999

[54] CERAMIC HEATER AND OXYGEN SENSOR

[75] Inventors: Takao Kojima; Yoshiaki Kuroki; Kunio Yanagi, all of Nagoya, Japan

[73] Assignee: NGK Spark Plug Co., Ltd., Nagoya, Japan

[21] Appl. No.: 08/837,126

[22] Filed: Apr. 14, 1997

Related U.S. Application Data

[63] Continuation of application No. 08/457,116, Jun. 1, 1995, abandoned.

[30] Foreign Application Priority Data

Jul. 6, 1994 [JP] Japan ................................ 6-154703

[51] Int. Cl.$^6$ .................................................. G01N 27/00
[52] U.S. Cl. ..................... 219/209; 219/538; 219/543; 219/552; 338/308; 73/31.05; 73/25.03; 204/426
[58] Field of Search .......................... 219/538, 209, 219/543, 546, 548, 552, 553, 544; 338/307–309, 34, 314; 204/424, 426; 73/25.03, 31.05, 204.11, 204.16, 204.17, 204.23, 204.26, 204.25

[56] References Cited

U.S. PATENT DOCUMENTS

| | | | |
|---|---|---|---|
| 1,731,120 | 10/1929 | Abbott | 219/544 |
| 1,975,410 | 10/1934 | Simpson | 373/134 |
| 2,725,453 | 11/1955 | Haller | 219/245 |
| 3,539,767 | 11/1970 | Eisler | 219/213 |
| 3,912,905 | 10/1975 | Giler | 219/464 |
| 4,453,397 | 6/1984 | Ohta et al. | 73/23.31 |
| 4,486,651 | 12/1984 | Atsumi et al. | 219/553 |
| 4,697,165 | 9/1987 | Ishiguro et al. | 338/34 |
| 4,785,150 | 11/1988 | Kojima et al. | 219/543 |
| 4,804,823 | 2/1989 | Okuda et al. | 219/553 |
| 4,806,739 | 2/1989 | Kojima et al. | 219/543 |
| 4,883,947 | 11/1989 | Murase et al. | 219/553 |
| 4,943,330 | 7/1990 | Iino et al. | 204/426 |
| 4,958,514 | 9/1990 | Takami et al. | 338/34 |
| 5,068,517 | 11/1991 | Tsuyuki et al. | 219/553 |
| 5,264,681 | 11/1993 | Nozaki et al. | 219/553 |

FOREIGN PATENT DOCUMENTS

| | | | |
|---|---|---|---|
| 3538460 | 4/1986 | Germany | 73/31.05 |
| 1-109221 | 4/1989 | Japan | 73/204.11 |
| 3-84423 | 4/1991 | Japan | 73/204.16 |
| 4-343022 | 11/1992 | Japan | 73/204.11 |

*Primary Examiner*—John A. Jeffery
*Attorney, Agent, or Firm*—Foley & Lardner

[57] ABSTRACT

A ceramic heater for heating a sensor such as an oxygen sensor has a ceramic substrate and a heater pattern formed on the substrate. A heater pattern 22 is tightly interposed between first and second alumina substrates 15 and 21. This heater pattern 22 has a meandering heating section 25 and a pair of leads 26 for connecting both ends of the heating section 25 to two terminals at the base side end. The heating section 25 is divided into a tip side subsection 25a located near the tip side end of the device, and a base side subsection 25b. Specifically, the wire width is made greater in the tip side subsection 25a than in the base side subsection 25b so that the resistance per unit length is lower in the tip side subsection 25a. The thus-designed heater section 25 produces a less amount of heat in the tip side subsection than in the base side subsection, and this distribution of heat generation can reduce the possibility of cracks and breakage of a wire.

30 Claims, 19 Drawing Sheets

TABLE 1

| | LOT NO. | RESISTANCE[Ω] | | | WIRE WIDTH [mm] | |
| --- | --- | --- | --- | --- | --- | --- |
| | | TOTAL | HEATING SECTION | | BASE REGION | TIP REGION |
| | | | BASE REGION | TIP REGION | LEAD ON ONE SIDE | |
| EMBODIMENT | 1 | 4.64 | 2.57 | 1.63 | 0.22 | 0.25 | 0.35 |
| | 2 | 4.65 | 2.48 | 1.73 | 0.22 | 0.275 | 0.32 |
| COMPARATIVE EXAMPLE | 3 | 4.60 | 2.38 | 1.78 | 0.22 | 0.3 | 0.3 |

TABLE 2

| | LOT NO. | T/S | 14VX 2000HOURS | 15VX 1000HOURS | 18VX 100HOURS |
|---|---|---|---|---|---|
| EMBODIMENT | 4 | 1.15 | 1 (3) | 3 (5) | 3 (7) |
| | 5 | 1.22 | 1 (0) | 0 (0) | 0 (1) |
| | 6 | 1.33 | 0 (0) | 0 (0) | 0 (0) |
| | 7 | 1.66 | 0 (0) | 0 (0) | 0 (0) |
| COMPARATIVE EXAMPLE | 8 | 1 | 10 (15) | 10 (21) | 10 (25) |

FIG.9A

TABLE 3

| | LOT NO. | RESISTANCE[Ω] | | | WIRE WIDTH [mm] | |
| --- | --- | --- | --- | --- | --- | --- |
| | | TOTAL | HEATING SECTION | | LEAD ON ONE SIDE | |
| | | | BASE REGION | TIP REGION | | BASE REGION | TIP REGION |

| | LOT NO. | TOTAL | BASE REGION | TIP REGION | LEAD ON ONE SIDE | BASE REGION | TIP REGION |
| --- | --- | --- | --- | --- | --- | --- | --- |
| EMBODIMENT | 9 | 4.36 | 1.10 | 1.06 | 1.1 | 0.225 | 0.4 |
| | 10 | 4.45 | 1.08 | 1.17 | 1.1 | 0.25 | 0.35 |
| | 11 | 4.54 | 1.07 | 1.27 | 1.1 | 0.275 | 0.32 |
| COMPARATIVE EXAMPLE | 12 | 4.5 | 1.0 | 1.30 | 1.1 | 0.3 | 0.3 |

FIG.9B

TABLE 4

| | LOT NO. | T/S | 14VX 2000HOURS | 15VX 1000HOURS | 18VX 100HOURS |
| --- | --- | --- | --- | --- | --- |
| EMBODIMENT | 13 | 1.15 | 1 (1) | 3 (3) | 3 (5) |
| | 14 | 1.22 | 1 (1) | 0 (0) | 0 (0) |
| | 15 | 1.33 | 0 (0) | 0 (0) | 0 (0) |
| | 16 | 1.66 | 0 (0) | 0 (0) | 0 (0) |
| COMPARATIVE EXAMPLE | 17 | 1 | 10 (10) | 10 (12) | 10 (18) |

FIG.10A

TABLE 5

| | LOT NO. | RESISTANCE [Ω] | | | RATIO OF LENGTH [%] C/A | WIRE WIDTH [mm] MIDDLE/LATERAL | WIRE SPACING [mm] MIDDLE/LATERAL |
| | | TOTAL | HEATING SECTION | | LEAD (ONE SIDE) | | | |
| | | | MIDDLE | LATERAL (ONE SIDE) | | | | |
|---|---|---|---|---|---|---|---|---|
| EMBODIMENT | 18-a | 4.60 | 0.32 | 2.28 | 0.22 | 20 | 0.3/0.3 | 0.35/0.35 |
| | -b | ↑ | 0.28 | 2.30 | ↑ | ↑ | 0.35/0.3 | ↑ |
| | -c | ↑ | 0.32 | 2.28 | ↑ | ↑ | 0.3/0.3 | 0.45/0.3 |
| | -d | ↑ | 0.28 | 2.30 | ↑ | ↑ | 0.35/0.3 | 0.35/0.3 |
| | 19-a | ↑ | 0.52 | 2.18 | ↑ | 30 | 0.3/0.3 | 0.35/0.35 |
| | -b | 4.62 | 0.46 | 2.22 | ↑ | ↑ | 0.35/0.3 | ↑ |
| | -c | 4.60 | 0.52 | 2.18 | ↑ | ↑ | 0.3/0.3 | 0.45/0.3 |
| | -d | 4.62 | 0.46 | 2.22 | ↑ | ↑ | 0.35/0.3 | 0.35/0.3 |
| | 20-a | 4.61 | 0.73 | 2.08 | ↑ | 40 | 0.3/0.3 | 0.35/0.35 |
| | -b | ↑ | 0.63 | 2.13 | ↑ | ↑ | 0.35/0.3 | ↑ |
| | -c | ↑ | 0.73 | 2.08 | ↑ | ↑ | 0.3/0.3 | 0.45/0.3 |
| | -d | 4.60 | 0.62 | 2.13 | ↑ | ↑ | 0.35/0.3 | 0.35/0.3 |
| | 21-a | 4.61 | 0.89 | 2.0 | ↑ | 50 | 0.3/0.3 | 0.35/0.35 |
| | -b | ↑ | 0.79 | 2.05 | ↑ | ↑ | 0.35/0.3 | ↑ |
| | -c | ↑ | 0.89 | 2.0 | ↑ | ↑ | 0.3/0.3 | 0.45/0.3 |
| | -d | 4.60 | 0.78 | 2.06 | ↑ | ↑ | 0.35/0.3 | 0.35/0.3 |
| | 22-a | 4.62 | 1.06 | 1.92 | ↑ | 60 | 0.3/0.3 | 0.35/0.35 |
| | -b | 4.61 | 0.93 | 1.98 | ↑ | ↑ | 0.35/0.3 | ↑ |
| | -c | 4.62 | 1.06 | 1.92 | ↑ | ↑ | 0.3/0.3 | 0.45/0.3 |
| | -d | 4.61 | 0.93 | 1.98 | ↑ | ↑ | 0.35/0.3 | 0.35/0.3 |
| | 23-a | 4.59 | 1.21 | 1.83 | ↑ | 70 | 0.3/0.3 | 0.35/0.35 |
| | -b | 4.62 | 1.08 | 2.91 | ↑ | ↑ | 0.35/0.3 | ↑ |
| | -c | 4.59 | 1.21 | 1.83 | ↑ | ↑ | 0.3/0.3 | 0.45/0.3 |
| | -d | 4.62 | 1.08 | 1.91 | ↑ | ↑ | 0.35/0.3 | 0.35/0.3 |
| | 24-a | 4.60 | 1.34 | 1.77 | ↑ | 80 | 0.3/0.3 | 0.35/0.35 |
| | -b | 4.62 | 1.20 | 1.85 | ↑ | ↑ | 0.35/0.3 | ↑ |
| | -c | 4.60 | 1.34 | 1.77 | ↑ | ↑ | 0.3/0.3 | 0.45/0.3 |
| | -d | 4.62 | 1.19 | 1.86 | ↑ | ↑ | 0.35/0.3 | 0.35/0.3 |
| | 25-a | 4.61 | 1.47 | 1.71 | ↑ | 90 | 0.3/0.3 | 0.35/0.35 |
| | -b | ↑ | 1.31 | 1.79 | ↑ | ↑ | 0.35/0.3 | ↑ |
| | -c | ↑ | 1.47 | 1.71 | ↑ | ↑ | 0.3/0.3 | 0.45/0.3 |
| | -d | ↑ | 1.32 | 1.78 | ↑ | ↑ | 0.35/0.3 | 0.35/0.3 |
| COMP. | 26 | 4.60 | 1.58 | 1.58 | ↑ | 100 | 0.3/0.3 | 0.35/0.35 |

NO.27

NO.28

NO.29

NO.30

TABLE 6

|  | LOT NO. | WIRE WIDTH [mm] | | |
| --- | --- | --- | --- | --- |
|  |  | LEAD | BASE REGION | TIP REGION |
| EMBODIMENT | 27 | 0.8 | 0.28 | 0.31 |
|  | 28 | ↑ | ↑ | 0.35 |
|  | 29 | ↑ | ↑ | 0.4 |
|  | 30 | ↑ | ↑ | 0.35 |
| COMPARATIVE EXAMPLE | 31 | ↑ | 0.3 | 0.3 |

CERAMIC HEATER AND OXYGEN SENSOR

This application is a continuation of application Ser. No. 08/457,116, filed Jun. 1, 1995 now abandoned.

BACKGROUND OF THE INVENTION

The present invention relates to a ceramic heater for a sensor such as an oxygen sensor used for internal combustion engines of motor vehicles, and to a self-heating type oxygen sensor having a ceramic heater.

A plate-shaped laminate ceramic heater having a heating element of Pt or W as a heater pattern in a ceramic substrate has been hitherto widely used for oxygen sensors, general purpose heaters or various other purposes.

FIGS. 18A and 18B show one conventional example. As shown in FIG. 18A, a plate-shaped sensor device 100 includes an oxygen sensor plate 102 having a gas sensing element 101 of metal oxide such as titania, and a ceramic heater plate 103 which are integrated into a single multilayer unit. The ceramic heater plate 103 has a ceramic substrate 107 on which, as shown in FIG. 18B, there is formed a heater pattern 106 consisting of a meandering heating section 104 and a lead section of a pair of leads 105 extending from the heating section 104.

However, this conventional heater 103 is disadvantageous in the following points.

When the oxygen sensing device 102 is enclosed in a metal case, there arises a temperature difference between the tip side portion and the base side portion of the ceramic substrate 107 because of the metal case drawing heat. The temperature of the tip side portion becomes lower by heat dissipation to the surrounding while on the other hand the temperature of the base side portion is decreased by heat conduction. The heat conduction is more effective, and accordingly the base side portion becomes lower in temperature. In consideration of this temperature decrease, this heater system is arranged to apply a relatively high voltage to maintain the temperature of the device in a predetermined range. If, however, an excessive voltage is applied beyond that, the tip side portion becomes excessively hot, so that the tip side portion tends to suffer wire breakage.

In the case of a laminate type sensor using a solid electrolyte of zirconia, application of an excessive voltage makes the tip side portion of the ceramic substrate excessively hot, so that the insulating ability becomes low, blackening occurs, and the performance become poor.

In recent OBD-II (On-Board Diagnosis) requirements for automobile exhaust emission control in the United States, a diagnostic system must detect degradation and malfunction of an oxygen sensor, a catalytic converter, other sensors of the control system, etc. The conventional device is not satisfactory in this point either.

This OBD-II is a regulation of an environmental protection law that will presumably become effective about 1996 in California. When exhaust emissions of an engine become unable to adapt to a restricted level, the OBD-II system must inform the driver that the emission control system has a malfunction. If the indication system for indicating this malfunction fails, this failure alone is regarded as a subject for recall. Therefore, the system for detecting deterioration of the oxygen sensor, catalytic converter and control sensors is important, and required to function accurately for a long time.

A system of one example therefore has a diagnostic oxygen sensor on the downstream side of the catalytic converter too. In this case, however, during an engine starting operation, condensed water collected in the catalytic converter is splashed in droplets, and attached to the gas sensitive element 101 heated by a heater on the downstream side of the catalytic converter, so that the sensitive element 101 can be damaged. Therefore, the system must postpone current supply to the heater by about 30 seconds after a start of the engine until the splash of the condensed water subsides significantly. This delay of the heating operation prolongs a time until the sensitive element reaches a proper temperature for activation. During this prolonged time, the air fuel ratio control is not accurate enough, resulting in degradation in the efficiency of exhaust decontamination and the fuel efficiency both.

In the case of the oxygen sensor provided on the downstream side of the catalytic converter, there is formed, between inner and outer tubes (8 and 9) of the oxygen sensor (as shown in FIG. 1), an annular space for protection against mechanical and thermal impact of stones and water flung and splashed by the front wheels. This structure increases the thermal capacity of the metal support of the oxygen sensor, and tends to further promote the heat conduction from the base portion of the ceramic heater.

It is thus required to heat the gas sensitive element 101 to the activating temperature as soon as possible. Since the ordinary air fuel ratio sensor on the upstream side of the catalytic converter reaches its activating temperature in about 50 sec after a start of the engine, it is specifically desired to activate the diagnostic oxygen sensor within this time, that is, after 20 sec or less from a start of current supply.

In order to rapidly heat the sensitive element, it is possible to apply a higher voltage on the ceramic heater 103 for the oxygen sensing device 102. In this case, however, a sharp temperature change causes a severer temperature difference between the tip side portion and the base side portion of the ceramic substrate 107, and this increases the undesired possibility of broken wire and blackening.

SUMMARY OF THE INVENTION

It is therefore an object of the present invention to provide a ceramic heater and an oxygen sensor which can heat a sensitive element more rapidly without incurring crack and breakage of a wire.

According to the present invention, a ceramic heater for a sensor such as an oxygen sensor, includes at least: a ceramic substrate such as an alumina substrate; and a heater pattern formed on said ceramic substrate. The heater pattern includes at least a lead section and a heating section which extends from said lead section. The heating section includes at least a base side subsection, and a tip side subsection having a resistance per unit length lower than that of said base side subsection. This heating section is thus designed to generate a less amount of heat in said tip side subsection than in said base side subsection.

An oxygen sensor according to the present invention comprises not only the ceramic heater but a sensing section having a gas sensitive element as well. The gas sensitive element may be a resistive type element made of a metal oxide, such as titania, having a resistance responsive to the percentage of oxygen in a gas mixture such as engine exhaust gases, or may be potentiometer type element of a solid electrolyte such as zirconia.

The resistance per unit length is made lower in said tip side subsection, for example, by increasing a wire width of said heating pattern in said tip side subsection of said heating section than in said base side subsection.

The thus-constructed ceramic heater according to the invention can prevent such overheat of the tip side portion as to break the heating element in the tip side portion, by preventing the temperature difference between the tip side portion and the base side portion from increasing even when a large amount of heat is absorbed from the base side portion by conduction, and a high voltage is applied to the heater.

BRIEF DESCRIPTION OF THE DRAWINGS

FIG. 9A is a table for showing features of samples used in the third experiment.

FIG. 9B is a table showing conditions and results of the fourth experiment.

FIG. 10A is a table showing features of samples used in a fifth experimental example for confirming effects of the third embodiment.

DETAILED DESCRIPTION OF THE INVENTION

First Embodiment

Figure 1:
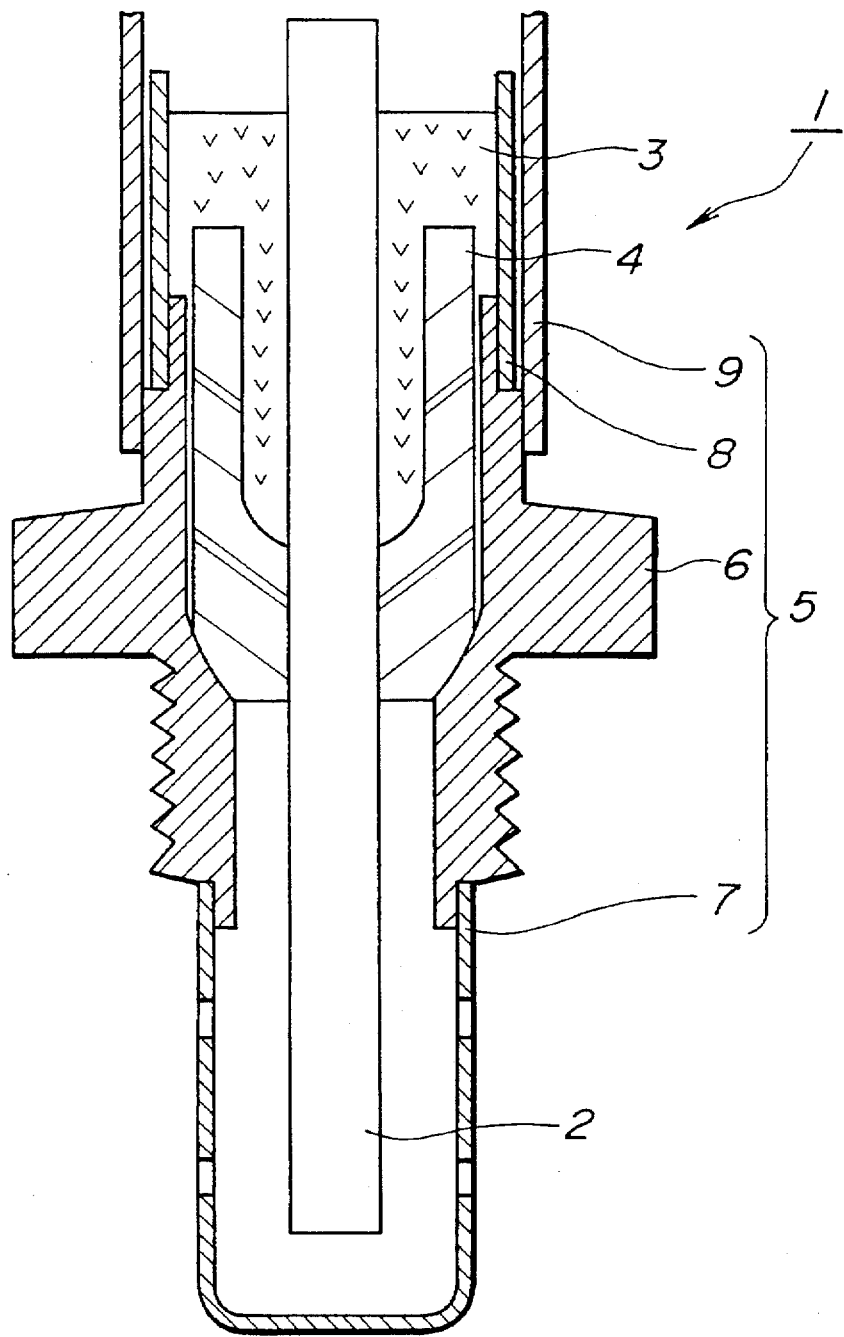
FIG. 1 is a sectional view showing an oxygen sensor of a first practical example according to a first embodiment of the present invention with a part cut away to show an interior structure.

FIG. 1 shows an oxygen sensor 1 having a ceramic heater according to a first embodiment of the present invention. The ceramic heater is integrally formed in an oxygen sensing device 2 of the oxygen sensor 1. The oxygen sensing device 2 is fixed in a metal case 5 through a glass seal 3 and a ceramic sleeve 4. The metal case 5 is constituted by a metal support member 6, a metal cap 7 mounted on one side (tip side or probe side) of the support member 6, and outer and inner tubes 8 and 9 mounted on the opposite side (base side) of the support member 6.

Figure 2:
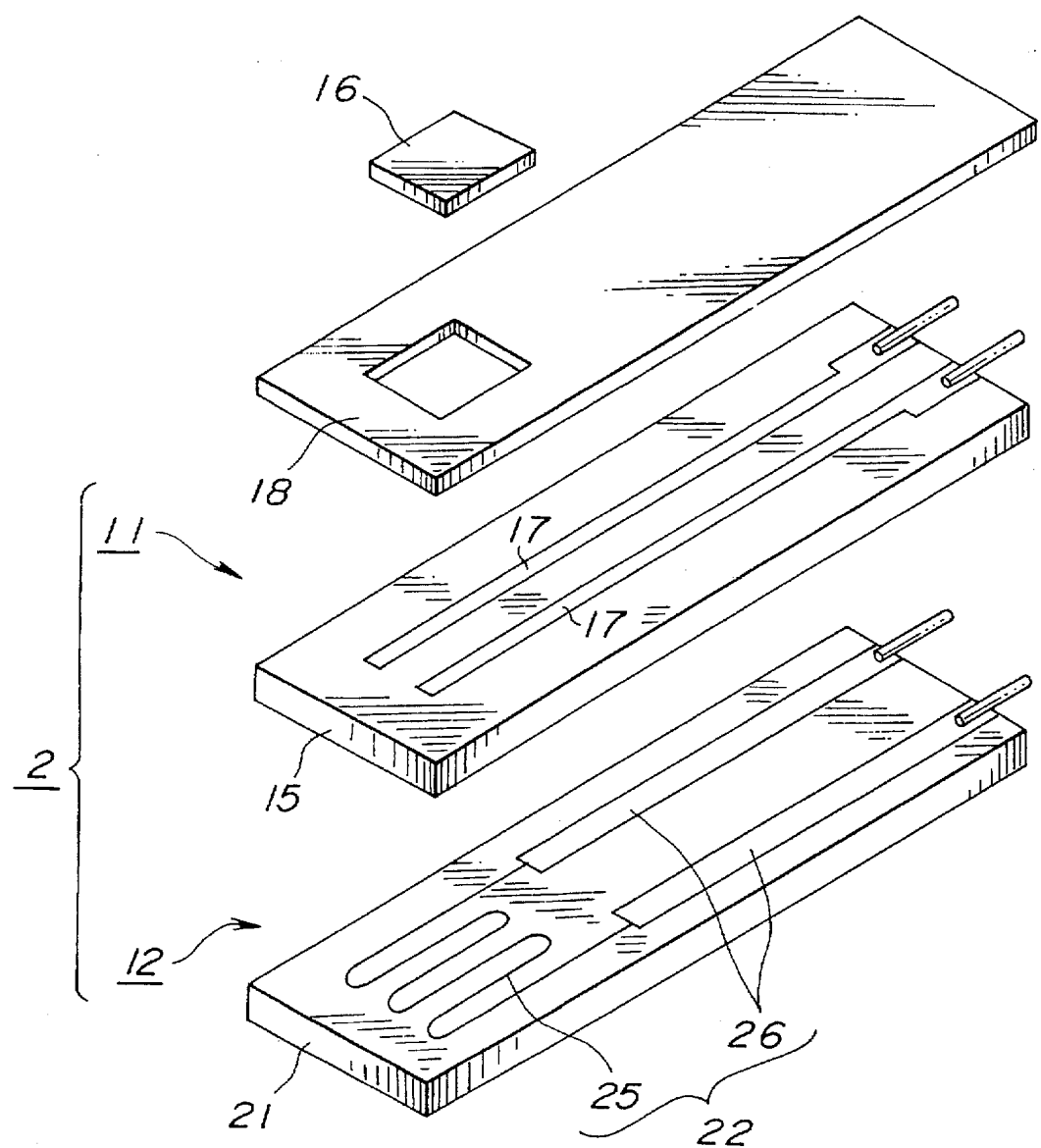
FIG. 2 is an exploded perspective view showing an oxygen sensing device of the oxygen sensor shown in FIG. 1.

As shown in FIG. 2, the oxygen sensing device 2 of this example is a columnlike device of 4 mm width×40 mm length×1.2 mm thickness. The sensing device 2 has a laminated structure of a sensor plate 11 having a thickness of 0.7 mm, and a ceramic heater plate 12 having a thickness of 0.5 mm.

The sensor plate 11 of this example consists of a first alumina substrate (sensor substrate) 15 of alumina (the purity of alumina is equal to or more than 85%) having a thickness of 0.5 mm, a gas sensitive element 16 of sensitive metal oxide such as titania, a pair of detecting electrodes 17 of Pt which are in contact with the sensitive element 16, and a 0.2 mm thick insulating sheet 18 of alumina or the like covering most of the electrodes 17. The insulating sheet 18 is designed to define an area (electrode area) in which the sensitive elements 16 and the electrodes 17 are in contact, and to seal the remainder other than the contacting portions of the sensitive element 16 and the electrodes 17, against an atmosphere. In this embodiment, the sensor plate 11, the detecting electrodes 17 and the sensitive element 16 serve as an oxygen sensing means, and the sensitive element 16 forms the oxygen sensing portion.

The ceramic heater plate 12 of this example consists of a 0.5 mm thick second alumina substrate 21, and a heater pattern 22 of Pt formed on the substrate 21.

In this example of the first embodiment, the heater pattern 22 is sandwiched between the first and second alumina substrates 15 and 21. A heating section 25 of the heater pattern 22, and the sensitive element 16 are situated substantially at the same position on the two opposite sides of the first alumina substrate 15.

Figure 3:
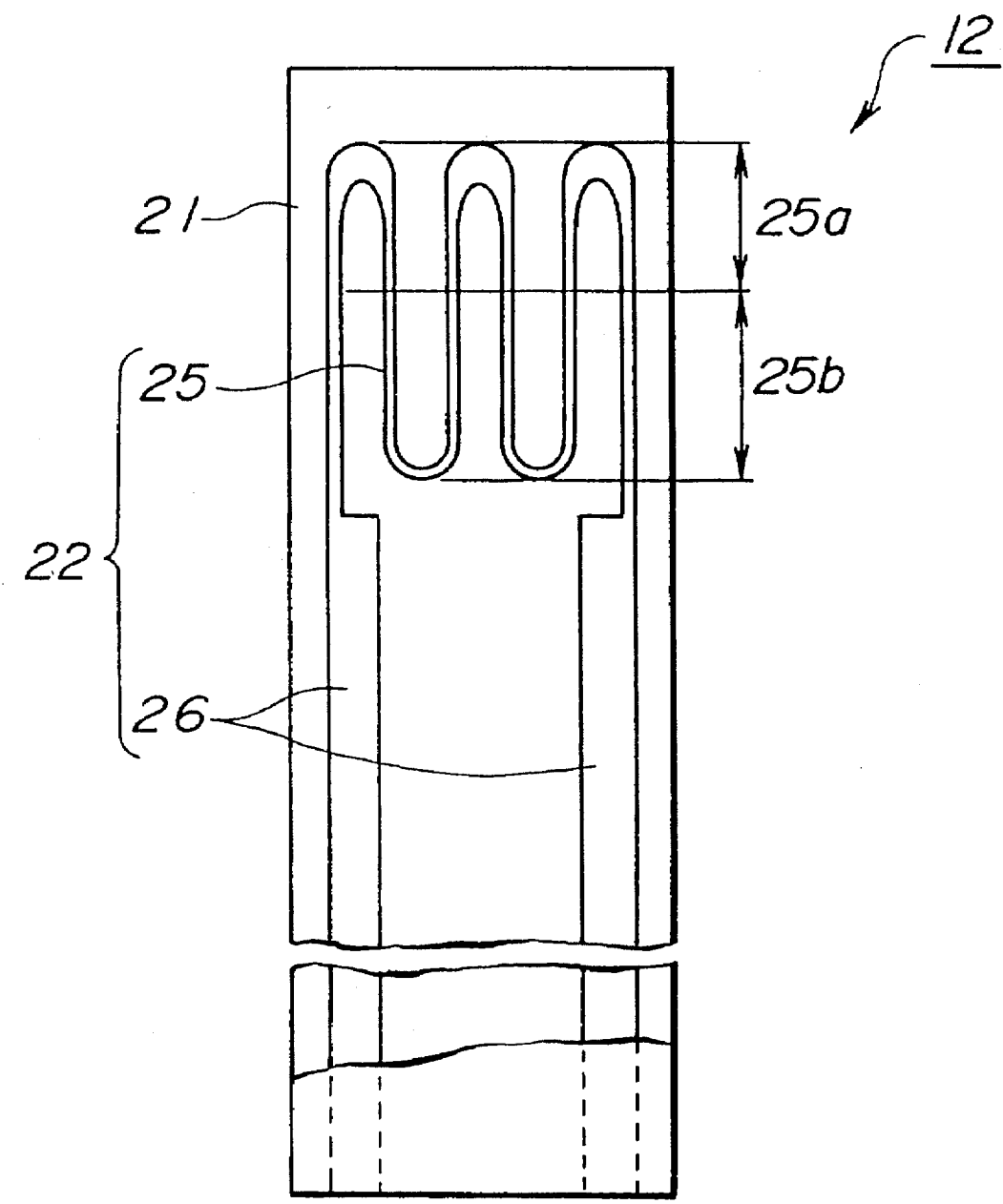
FIG. 3 is a plan view of a ceramic heater in the oxygen sensing device shown in FIG. 2.

As shown in FIG. 3, the heater pattern 22 formed on the second alumina substrate 21 comprises the above-mentioned heating section 25, and a lead section consisting of a pair of leads 26. Near a tip side end of the second alumina substrate 21, the heating section 25 meanders so as to form six line segments which, in this example, are straight, parallel to each other, parallel to the longitudinal direction of the second alumina substrate 21 and regular in line spacing. The left and right (or first and second) leads 26 extend from left and right (or first and second) ends of the heating section 25 toward a base side end of the second alumina substrate 21 along the longitudinal direction of the substrate 21.

As shown in FIG. 3, the heating section 25 is in the form of a wire extending sinuously in both a tip side region 25a and a base side region 25b. In this example, a wire width (or line width) of the heating section 25 in the tip side region 25a and a wire width in the base side region 25b of the heating section 25 are so determined that a resistance per unit length in the tip side portion 25a is smaller than that in the base side portion 25b.

<First Experimental Example>

In the following, an explanation is made on a first experiment performed to confirm effects of the ceramic heater design according to the first embodiment.

This experimental example employs the ceramic heater design according to the first embodiment. Namely, each of samples prepared for use in this experiment is in the form of a ceramic heater unit (4.0 mm width×40.0 mm length×1.0 mm thickness) in which the heater pattern 22 is tightly interposed between the first alumina substrate 15 and the second alumina substrate 21.

In these samples, the leads 26 are 28 mm long along the longitudinal direction, the heating section 25 is 10 mm long along the longitudinal direction, and the meandering portion of the heating section 25 is 9 mm long along the longitudinal direction. The heating section 25 has a tip side subsection in the tip side region 25a and a base side subsection in the base side region 25b. The tip side subsection 25a having a greater wire width is 4 mm long, and the base side subsection 25b having a smaller wire width is 5 mm long along the longitudinal direction. As shown in Table 1 of FIG. 4A, the samples prepared are classified into three groups identified by Lot Nos. 1, 2 and 3. The samples in each lot were prepared under identical conditions. Each of the three lots contains 25 samples. In the first and second lots (Lot Nos. 1 and 2), the wire width (that is, the resistance value) of the tip side subsection 25a is differentiated from that of the base side subsection 25b according to the first embodiment of the present invention. The third lot (No. 3) is a comparative example in which the wire width (line width) is the same between the tip side subsection 25a and the base side subsection 25b. Each of the resistance values listed in Table 1 is an average of values of the 25 samples in one of the lots.

Figures 4, 4A:
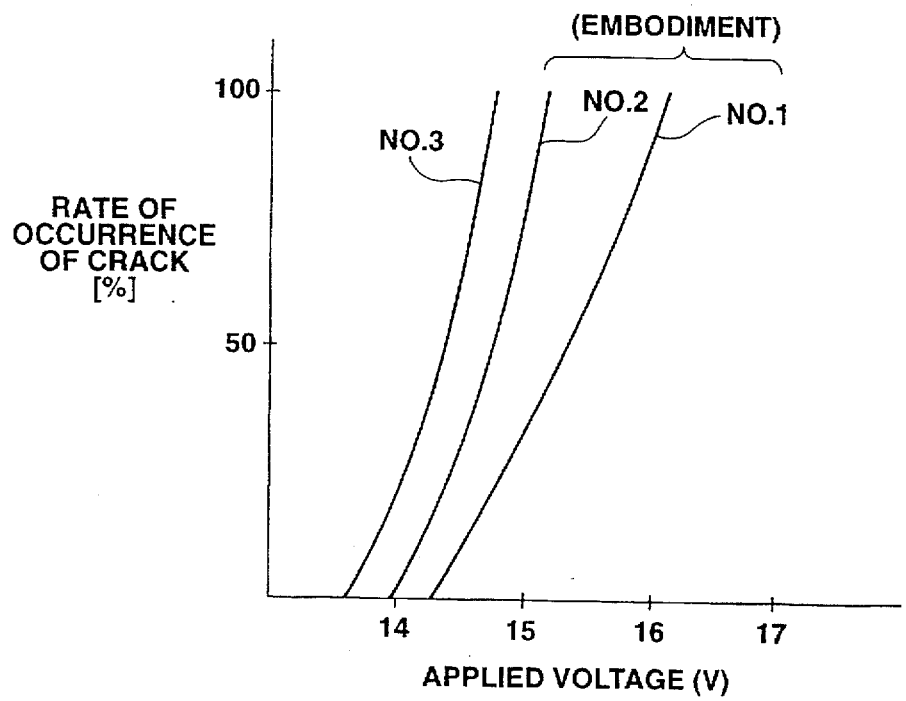
FIG. 4 is a graph showing the results of a first experiment to illustrate how a rate of occurrence of crack is reduced by the design of the first example according to the first embodiment.
FIG. 4A is a table for showing features of samples used in the first experiment.

The heater resistances (total resistances) of the ceramic heaters of these samples are made equal to about 4.6 Ω. In this experiment, it is examined whether cracks are formed in the heaters as a result of application of a predetermined DC voltage for 20 seconds at a normal temperature in the atmosphere. First, a voltage of 13.5 Vdc is applied for 20 seconds. After that, the applied voltage is turned off, and each sample is allowed to cool spontaneously to the normal temperature. This on-off cycle of application of 13.5 Vdc and spontaneous cooling is repeated 100 times. If no crack is formed in the ceramic heater substrate by the hundred on-off cycles at 13.5 Vdc, then the applied voltage is increased by 0.5 Vdc and the on-off cycle at the increased voltage level is repeated 100 times in the same manner. In this way, the applied DC voltage is increased stepwise by 0.5 V each time. FIG. 4 shows the results of this test. To examine cracks, use is made of water-soluble red ink, or alcohol colored with red ink.

As evident from FIG. 4, the samples according to this embodiment of the present invention are superior in that the rate of occurrence of cracks is relatively low even when the applied voltage is high. Specifically, the lower the resistance of the tip side subsection 25a is (as the samples of the first lot), the less likely a crack is to occur. By contrast to this, the samples of the comparative example is more likely to suffer cracks even when the applied voltage is low.

<Second Experimental Example>

Figures 5, 5A:
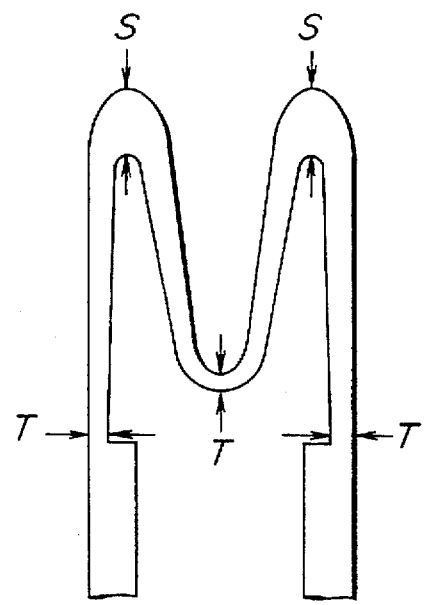
FIG. 5 is a plan view showing a heater pattern of a second practical example according to the first embodiment.
FIG. 5A is a table showing results of a second experiment for confirming effects of the second practical example according to the first embodiment.

In this experiment, ceramic heater samples (4.0 mm wide, 40.0 mm long, and 1.0 mm thick) were prepared which each have the heater pattern as shown in FIG. 5, inserted between the first and second alumina substrates 15 and 21.

The heater pattern of FIG. 5 has the heating section which meanders so as to form four line segments. The heating section of FIG. 5 is thick in the wire width in the tip side region, and has resistivity S [resistance Ω/length L] in the tip side region. In the base side region, the heating section of FIG. 5 is thin in the wire width and its resistivity is T [Ω/L]. The prepared ceramic heater samples have different values of the ratio T/S as shown in Table 2 of FIG. 5A. Each of five groups (Lot Nos. 4–8) includes 25 samples. In the lot numbers 4–7, the resistivity S in the tip side region is smaller than the resistivity T in the base side region, and the ratio T/S is greater than one, as shown in Table 2. The lot number 8 is a comparative example in which the wire width is not made different, and the resistivity S in the tip side region is equal to the resistivity T in the base side region.

The heater resistances (total resistances) of the ceramic heaters of these samples are made equal to about 4.6 Ω. In this experiment, voltages of different magnitudes (14, 15 and 18 V) are applied for different time durations (2000, 1000 and 100 hours) as shown in Table 2 in the atmosphere at the normal temperature, and the numbers of occurrences of crack and breakage of wire are checked. The results are listed in Table 2 of FIG. 5A. This table lists the numbers of the samples having wire broken without parentheses, and the number of the samples spoiled with crack within parentheses.

As evident from Table 2, the samples (Nos. 4~7) designed to generate a smaller amount of heat in the tip side region than in the base side region are less likely to suffer cracking and breaking of wire even when the predetermined voltage is applied for a long time. This advantageous effect increases as the ratio T/S is increased. Specifically, the effect is remarkable when T/S is greater than 1.22. In the samples of the comparative example (No. 8), by contrast, cracks and wire breakage are generated under all the test conditions.

Second Embodiment

Figure 6:
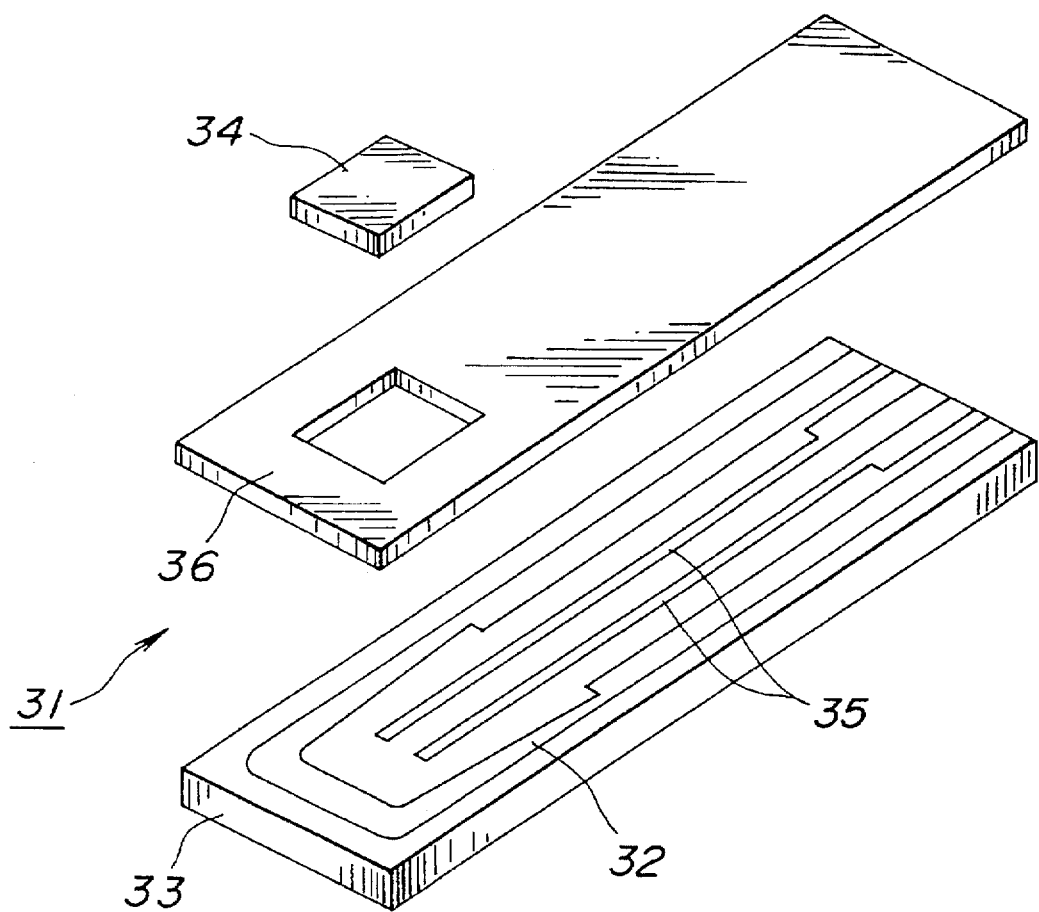
FIG. 6 is an exploded perspective view of an oxygen sensing device according to a second embodiment.

FIG. 6 shows one example according to a second embodiment of the present invention. A plate-like oxygen sensing device 31 shown in FIG. 6 is 4 mm wide, 40 mm long and 1.2 mm thick. A heater pattern 32 for heating this oxygen sensitive device 31 is significantly different in shape and position from that according to the first embodiment.

The sensing device 31 shown in FIG. 6 comprises an alumina substrate 33 having a thickness of 1 mm, a gas sensitive element 34 of titania or the like, mounted on the alumina substrate 33, an output takeout section which, in this embodiment, includes a pair of detecting electrodes 35 of Pt formed on the alumina substrate 33, and an insulating sheet 36 having a thickness of 0.2 mm and covering the electrodes 35 (except for the area of the sensitive element 34). The heater pattern 32 according to the second embodiment is formed on the same surface of the alumina substrate 33 on which the detecting electrodes 35 are formed. The heater patter 32 extends around the electrodes 35 so that the electrodes 35 are surrounded by the heater pattern 32 in the surface of the substrate 33.

Figure 7:
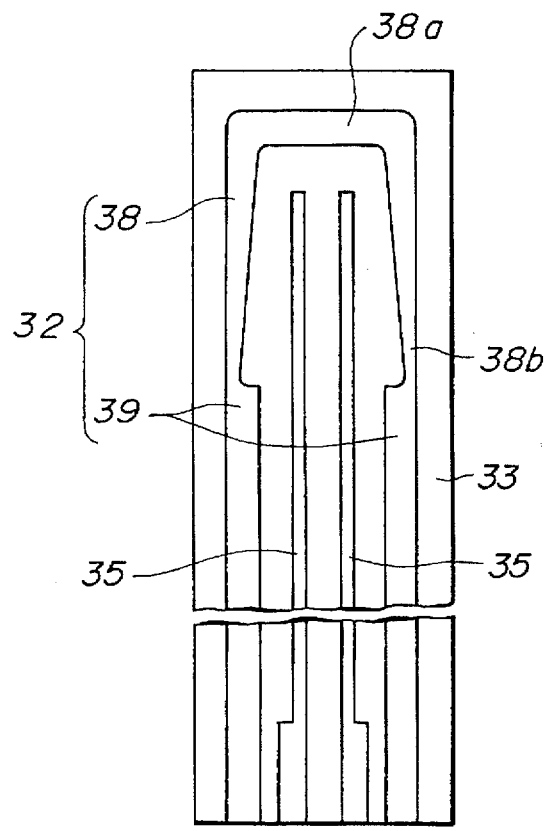
FIG. 7 is a plan view showing a ceramic heater in the oxygen sensing device of FIG. 6.

As shown in FIG. 7, the heater pattern 32 formed on the alumina substrate 33 has a heating section 38 extending in the shape of a letter U so as to surround the sensitive element 34 near the tip end of the alumina substrate 33, and a pair of leads 39 extending, respectively, from the left and right ends of the heating section 38, longitudinally to the base end of the substrate 33.

In this example, the heating section 38 has a tip side subsection 38a and a base side subsection 38b, and the resistance of the tip side subsection 38a is made smaller than that of the base side subsection 38b by making the wire width (line width) of the tip side subsection 38a greater than the wire width of the base side subsection 38b. Therefore, the heating section 38 produces less heat in the tip side region than in the base side region.

<Third Experimental Example>

In the following, an explanation is made on a third experiment performed to confirm effects of the ceramic heater design according to the second embodiment. In each of ceramic heater samples (having a width of 4.0 mm, a length of 40.0 mm and a thickness of 1.0 mm) for this experiment, the heater pattern is sandwiched between two alumina substrates (excluding the detecting electrodes).

Figure 8A:
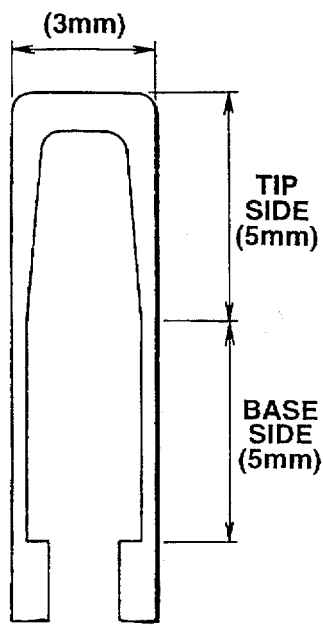
FIG. 8A is a plan view showing a heater pattern according to the second embodiment, used in a third experimental example for confirming effects of the second embodiment.

As shown in FIG. 8A, the ceramic heater used in this experiment has the leads which are 28 mm long along the longitudinal direction, and the heating section which is 10 mm long along the longitudinal direction. The heating section is 3 mm long along the lateral (widthwise) direction of the substrate as shown in FIG. 8A. In the heating section, the tip side subsection having a larger wire width is 5 mm long along the longitudinal direction, and the base side subsection having a smaller wire width is 5 mm long along the longitudinal direction. The wire width (i. e. the resistance) was differentiated between the tip side region and the base side region as shown in Table 3 of FIG. 9A in three groups (Nos. 9–11) each consisting of 25 identical samples. As a comparative example, 25 samples were further prepared in which the wire width is the same between the tip side region and the base side region.

Figure 9:
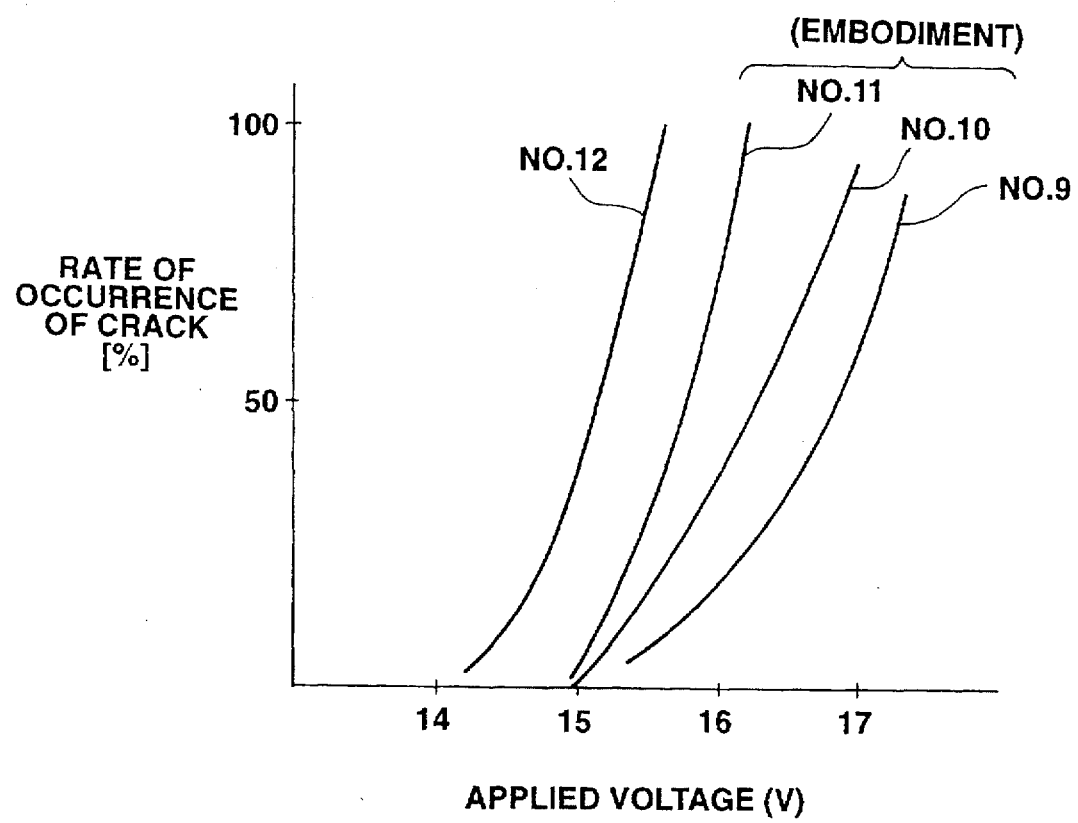
FIG. 9 is a graph showing the results of the third experimental example.

The heater resistance (total resistance) of each ceramic heater of these samples is made equal to about 4.5 Ω. In this experiment, it is examined whether cracks are formed in the heaters as a result of application of a predetermined DC voltage for 20 seconds at the normal temperature in the atmosphere. The test procedure is the same as the first experimental example. That is, the DC voltage is applied in on-off cycles at the level increased from 13.5 V, stepwise by 0.5 V each time. FIG. 9 shows the results of this test.

As evident from FIG. 9, the samples according to this embodiment is superior in that the rate of occurrence of cracks is relatively low. Specifically, the lower the resistance of the tip side subsection is, the less subject the heater is to a crack. By contrast to this, the samples of the comparative example is more likely to suffer cracks even when the applied voltage is low.

<Fourth Experimental Example>

In this experiment, there are prepared ceramic heater samples (4.0 mm wide, 40.0 mm long, and 1.0 mm thick) each having a U-shaped heater section. In each sample, a heater pattern as shown in FIG. 8B is sandwiched between two alumina substrates.

Figure 8B:
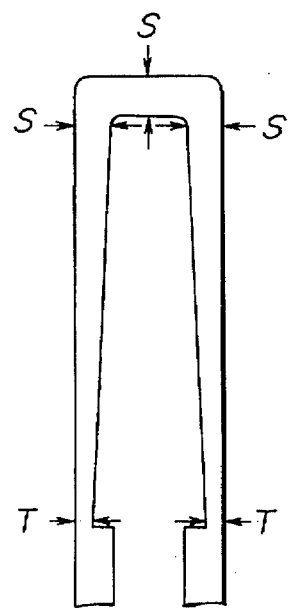
FIG. 8B is a plan view showing a heater pattern according to the second embodiment, used in a fourth experimental example.

In the heating section of, the heater pattern of FIG. 8B, the wire width (line width) in the tip side region is greater and its resistivity is S [Ω/L]. In the base side region, the heating section of FIG. 8B is smaller in the wire width and its resistivity is T [Ω/L]. The prepared ceramic heater samples have different values of the ratio T/S as shown in Table 4 of FIG. 9B. Each of the five groups (Lot Nos. 13~17) includes 25 identical samples. In the lot numbers 13–16, the resistivity S in the tip side region is smaller than the resistivity T in the base side region, and the ratio T/S is greater than one, as shown in Table 4. The lot number 17 is a comparative example in which the resistivity S in the tip side region is equal to the resistivity T in the base side region.

The heater resistances (total resistances) of the ceramic heaters of these samples are made equal to about 4.5 Ω. In this experiment, voltages of different magnitudes are applied for different time durations as shown in Table 4 in the atmosphere at the normal temperature, and the numbers of occurrences of cracks and breaking of wire are checked. The results are listed in Table 4 of FIG. 9B. The table lists the numbers of the samples having wire broken without parentheses, and the number of the samples spoiled with crack within parentheses.

As evident from Table 4, the samples (Nos. 13–16) designed to generate a smaller amount of heat in the tip side region than in the base side region are less likely to suffer cracking and breaking of wire even when the predetermined voltage (14, 15 or 18 V) is applied for long time. This advantageous effect increases as the ratio T/S is increased. Specifically, the effect is remarkable when T/S is greater than 1.22. In the samples of the comparative example (No. 17) where T/S=1, by contrast, cracks and wire breakage are generated under all the test conditions, as shown in Table 4.

Third Embodiment

A ceramic heater according to the third embodiment is integrally formed in an oxygen sensing device similar to that of the first embodiment.

The oxygen sensing device has a sensor plate and a ceramic heater plate which are both similar in dimensions to those shown in FIG. 2. The sensor plate includes a gas sensitive element, a pair of detecting electrodes, an insulating sheet and a first alumina substrate like the sensor plate 11 shown in FIG. 2. The ceramic heater plate having a heater pattern on a second alumina substrate is affixed to the back side of the sensor plate as in the first embodiment.

Figure 10:
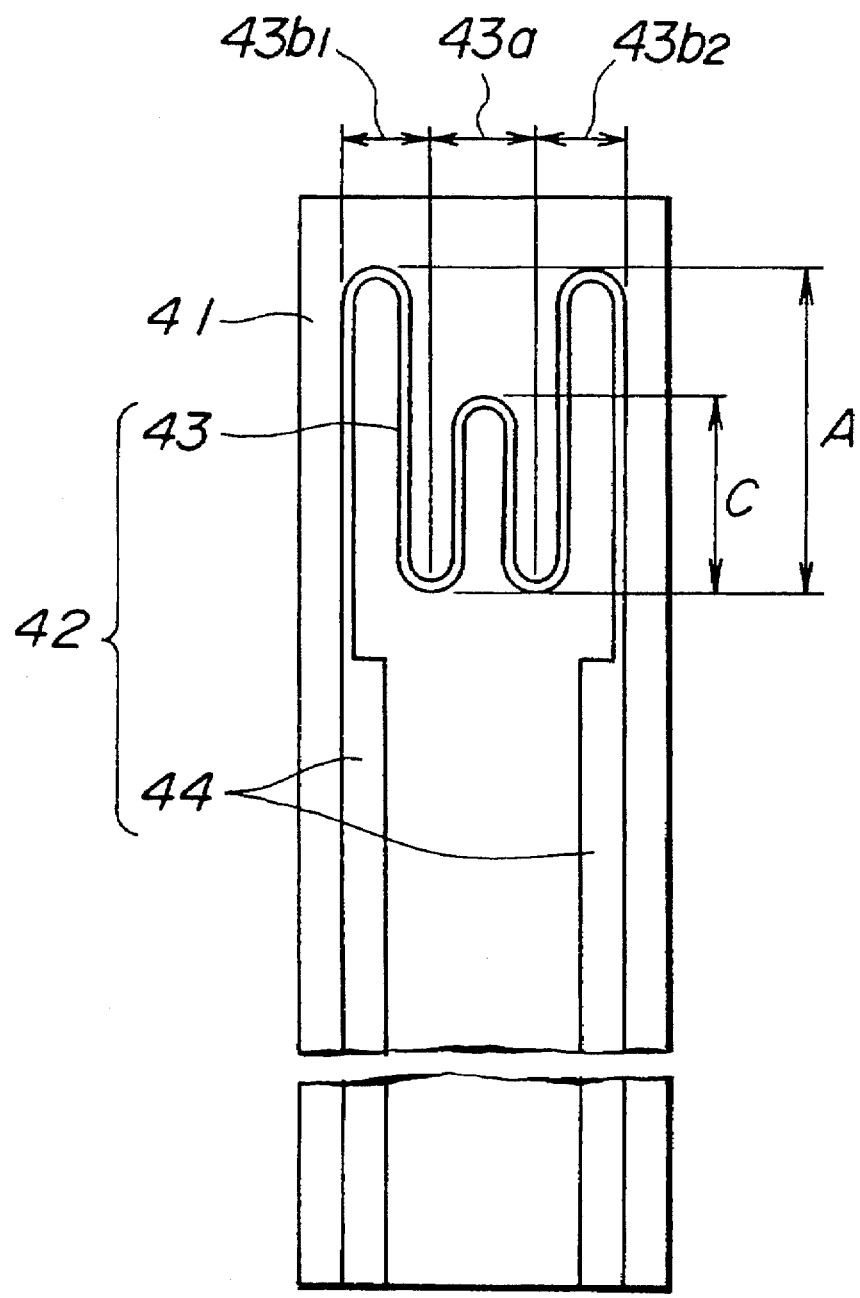
FIG. 10 is a plan view showing a ceramic heater according to a third embodiment of the present invention.

As shown in FIG. 10, the heater pattern 42 according to the third embodiment formed on the second alumina substrate 41 has a heating section 43, and left and right leads 44 extending from the left and right ends of the heating section 43, respectively, longitudinally to the base side end of the second alumina substrate 41. The heating section 43 meanders so as to form six line segments.

Figure 10B:
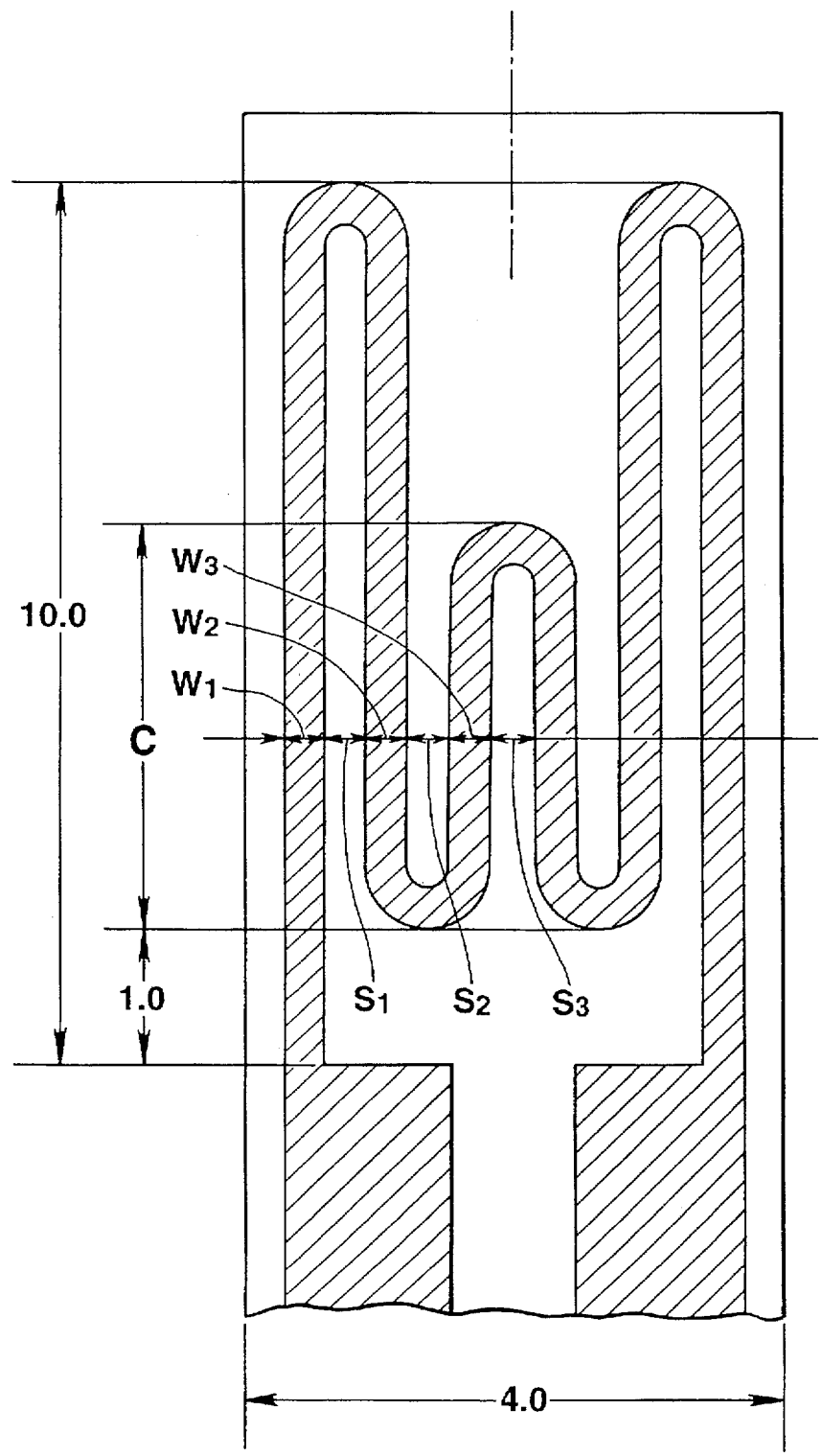
FIG. 10B is an enlarged plan view showing a heating section of the ceramic heater of FIG. 10.

The heating section 43 shown in FIG. 10 and shown more in detail in FIG. 10B has a middle subsection 43a, and left and right (first and second) lateral subsection 43b1 and 43b2. The middle subsection 43a is situated between the left and right subsection 43b1 and 43b2 along the lateral (widthwise) direction of the second substrate 41. In the example shown in FIGS. 10 and 10B, the heater pattern is substantially bilateral-symmetrical with respect to a longitudinal center line of the substrate 41. The longitudinal dimension C of the middle subsection 43a is smaller than the longitudinal dimension A of the left and right lateral subsection 43b1 and 43b2, as shown in FIG. 10. Moreover, the middle subsection 43a is formed only in the base side region whereas the lateral subregions 43b1 and 43b2 extend over both of the tip side region and the base side region. In the example shown in FIG. 10, the heating section 43 comprises four long straight line segments and two short straight line segments which are all regularly arranged in parallel to each other. The two short straight line segments belong to the middle subsection 43a, and each of the left and right lateral subsection 43b1 and 43b2 contains two of the four long straight line segments. In the tip side region, the left and right lateral subsections 43b1 and 43b2 are spaced apart along the lateral direction by a blank region where no heating element exists. Thus, the resistance of the middle subsection 43a is smaller than the resistance of each of the left and right lateral subsections 43b1 and 43b2. With this design, the heating section 43 produces more heat in the base side region and less heat in the tip side region which is situated longitudinally between the tip side end of the substrate 41 and the base side region.

The ratio C/A [%] between the longitudinal dimension C of the middle subsection 43a and the longitudinal dimension A of each of the left and right lateral subsections 43b1 and 43b2 is preferably in a range of $20 \leq C/S \leq 80$, as known from the following experimental example. A more desirable range of the ratio C/A is; $30 \leq C/S \leq 70$.

<Fifth Experimental Example>

A fifth experiment was performed to confirm effects of the ceramic heater according to the third embodiment of the present invention.

Each ceramic heater sample (4.0 mm wide, 40.0 mm long and 1.0 mm thick) has a heater pattern between first and second alumina substrates. The longitudinal dimension of the leads is 28 mm, the longitudinal dimension of the heating section is 10 mm, and the longitudinal dimension of the meandering portion of the heating section (that is, the longitudinal dimension A of the lateral subsections) is 9 mm. A longitudinal dimension is a dimension along the longitudinal direction of the substrate 41. As listed in Table 5 of FIG. 10A, there are 32 different sample groups (Lot Nos. 18-a~25-d) according to this embodiment and one group (No. 26) of a comparable example. Each sample group contains substantially identical 25 samples. The 32 groups are classified into eight categories each of which has a unique one of 8 different values of the ratio C/A (20, 30, 40, . . . 90) and contains four groups (18-a, 18-b, 18-c and 18-d, or 19-a, 19-b, 19-c and 19-d, or , or 25-a, 25-b, 25-c and 25-d). Thus, the total number of the groups according to the embodiment is 8×4=32. The suffix "a", as in 18-a, 19-a, . . . , indicates that the wire width (or line width) and wire spacing (or line spacing) are both the same between the middle subsection and the lateral subsections. In the sample groups identified by the suffix "b", the wire width is greater in the middle subsection than in the lateral subsections, and the wire spacing is the same between the middle subsection and the lateral subsections. The suffix "c" is to indicate that the wire width is the same between the middle and lateral, and the wire spacing is wider in the middle than in the lateral subsections. The suffix "d" indicates that the wire width and wire spacing are both made greater in the middle subsection.

The longitudinal dimension A of the left and right lateral subsections is 9.0 mm while the longitudinal dimension C of the middle subsection 43a is 1.8; 2.7; 3.6; 4.5; 5.4; 6.3; 7.2; 8.1; and 9.0, respectively, in the lot numbers 18-x (where x is a, b, c or d), 19-x, . . . 25-x, and 26. In the lot numbers 18-a~25-a and 26, the wire widths $W_1$, $W_2$ and $W_3$ (μm) and the wire spacings $S_1$, $S_2$ and $S_3$ (μm) shown in FIG. 10B are: $W_1$=300, $S_1$=350, $W_2$=300, $S_2$=350, $W_3$=300 and $S_3$=350. In the lot numbers 18-b~25-b; $W_1$=300, $S_1$=350, $W_2$=300, $S_2$=350, $W_3$=350 and $S_3$=350. In the lot numbers 18-c~25-c, $W_1$=300, $S_1$=300, $W_2$=300, $S_2$=300, $W_3$=300 and $S_3$=450. In the lot numbers 18-d~25-d, $W_1$=300, $S_1$=300, $W_2$=300, $S_2$=300, $W_3$=350 and $S_3$=350.

The heater resistance (total resistance) of each sample is about 4.6 Ω. The following items were examined.

(i) Examination of crack

Figure 11:
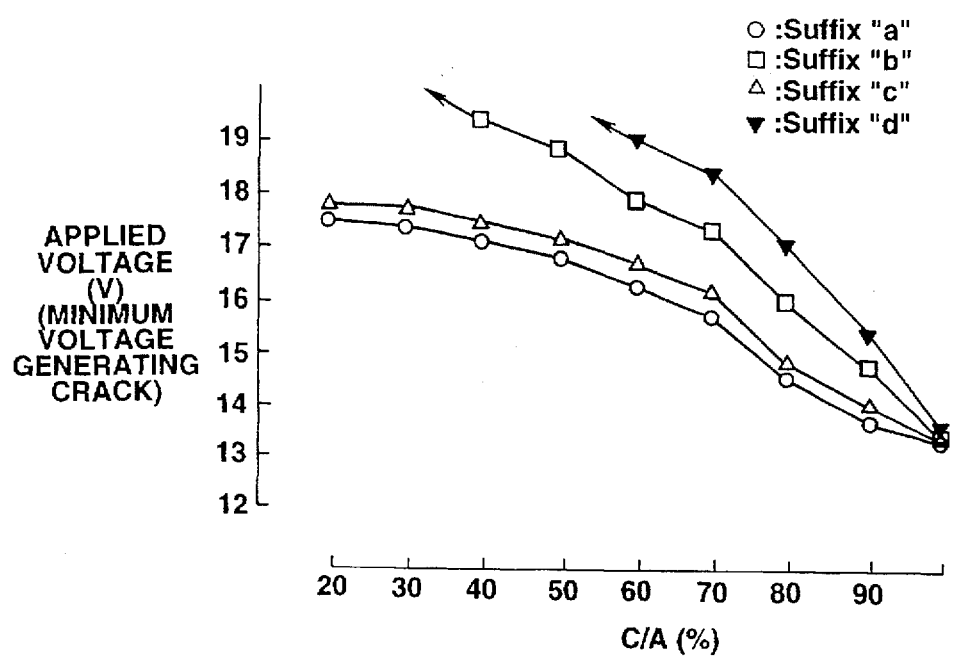
FIG. 11 is a graph showing results of crack examination of ceramic heater samples in a fifth experimental example for the third embodiment.

A predetermined DC voltage is applied to each sample for 60 seconds at the normal temperature in the atmosphere. First, a voltage of 10 Vdc is applied. After that, the applied voltage is turned off, and each sample is allowed to cool spontaneously to the normal temperature. This on-off cycle of an on period of voltage application and an off period of spontaneous cooling is repeated 100 times. If no crack is formed in the ceramic heater substrate by the hundred on-off cycles, then the applied voltage is increased by 0.5 Vdc and the on-off cycle at the increased voltage level is repeated 100 times in the same manner. In this way, the applied DC voltage is increased stepwise by 0.5 V each time. Then, it is examined whether a crack is formed in the heater substrate (that is, the minimum voltage at which a crack is produced). FIG. 11 shows the results of this examination.

(ii) Examination of wire breakage

Figure 12:
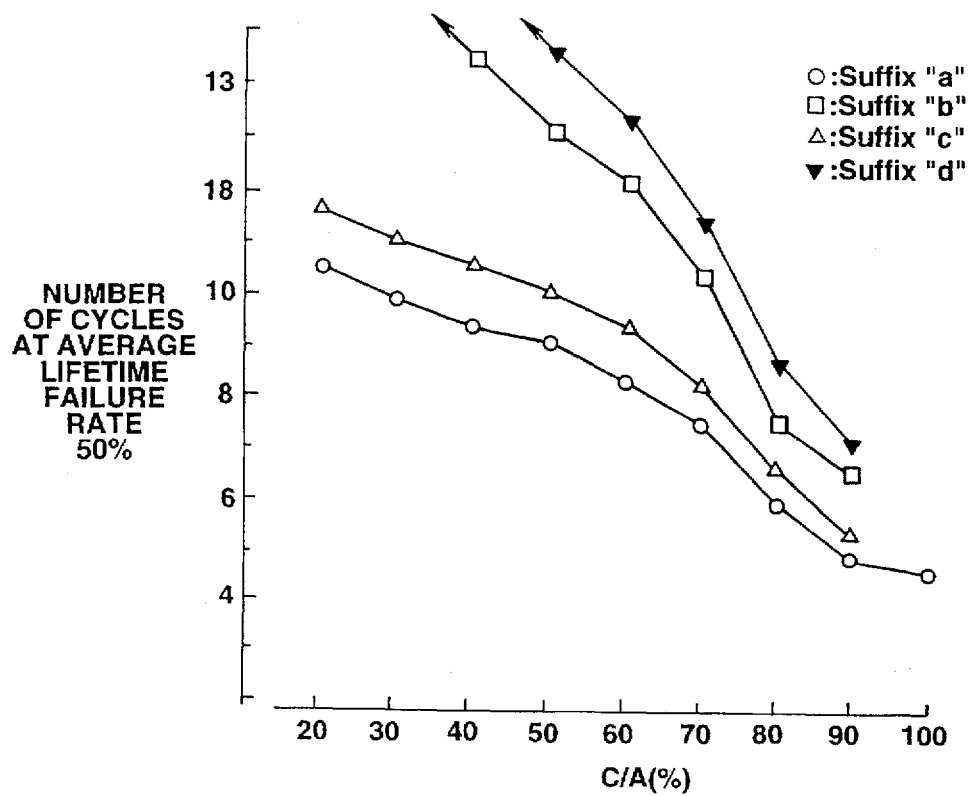
FIG. 12 is a graph showing results of wire breakage examination of the ceramic heater samples of the fifth experimental example.

An on and off cycle of an on period for application of a predetermined DC voltage for 60 seconds and an off period is repeated in the atmosphere at the normal temperature, and a check is made on the number of cycles required to cause the quantity in which the heater wire is broken amounts to 50%. FIG. 12 shows the results of the examination.

(iii) Examination on lateral temperature distribution

Figure 13:
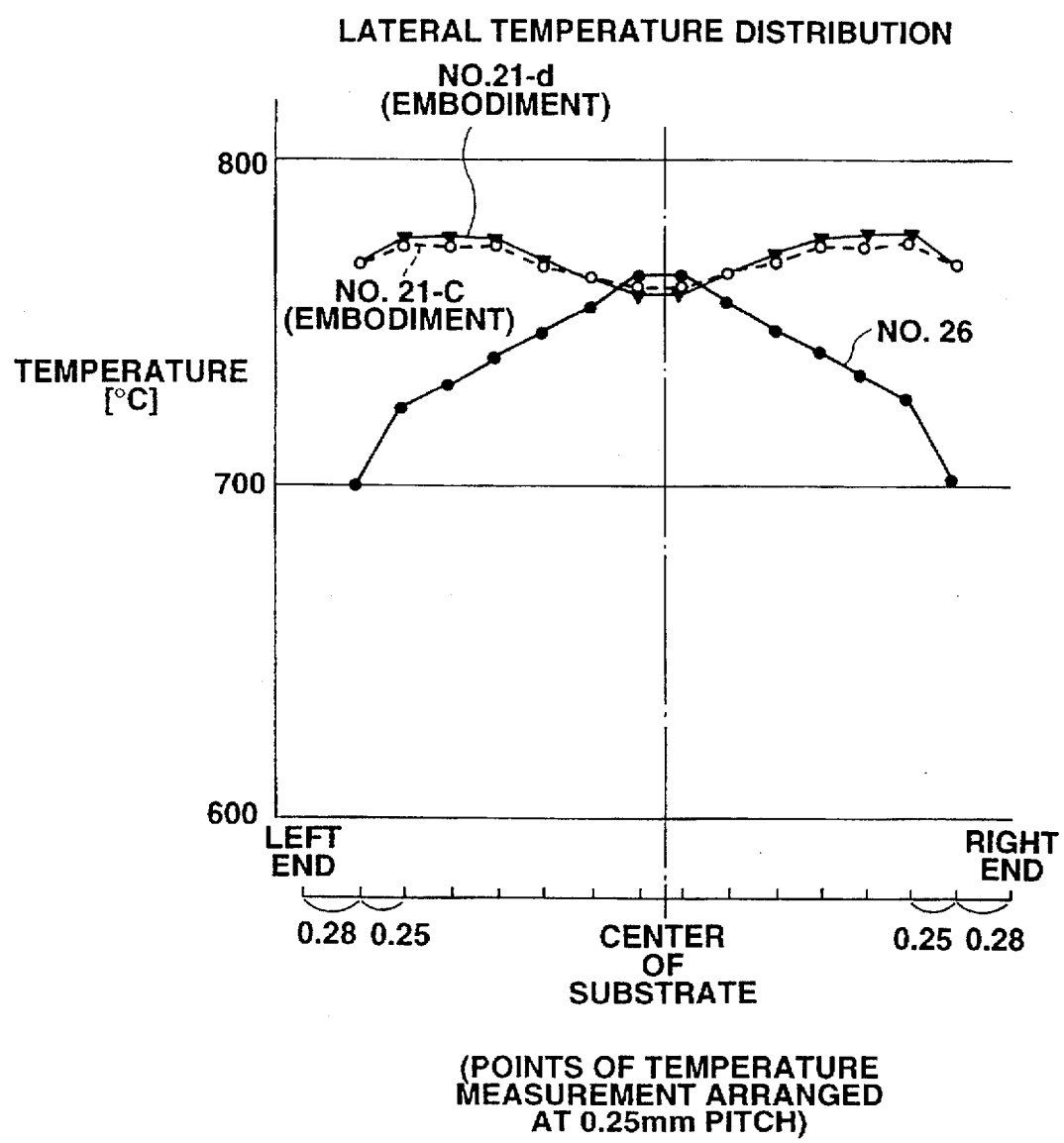
FIG. 13 is a graph showing a lateral temperature distribution in the ceramic heater samples of the fifth experimental example.

A temperature distribution along the lateral (widthwise) direction is examined in the samples of No. 21-c of the embodiment, and No. 26 of the comparative example. In this case, the temperature is measured along a lateral center line extending laterally through the center of the gas sensitive element 16 shown in FIG. 2 with an infrared radiation thermometer (manufactured by Nihon Denki Sanei Kabushiki Kaisha (Corp.)(Model No. TH-1100). FIG. 13 shows the results.

(iv) Examination on longitudinal temperature distribution

Figure 14:
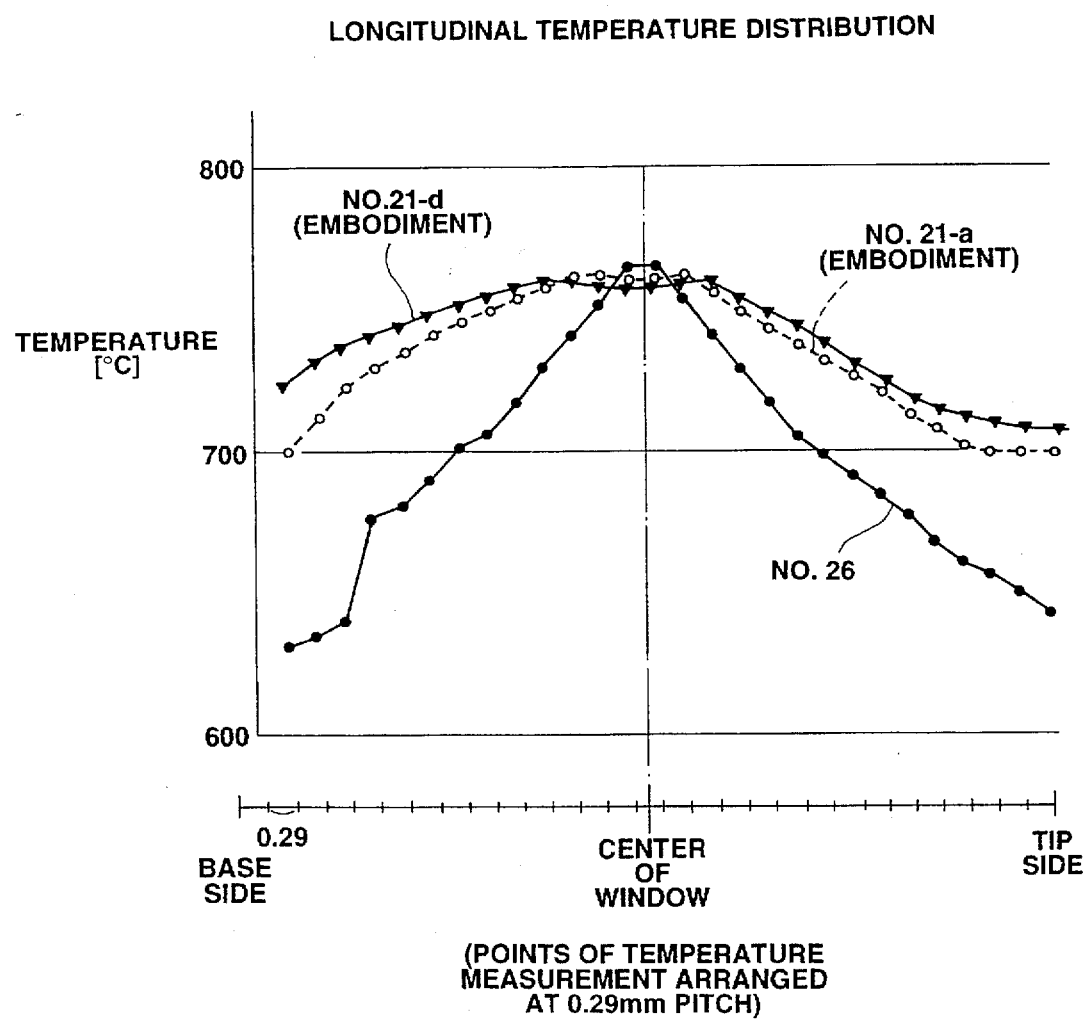
FIG. 14 is a graph showing a longitudinal temperature distribution in the ceramic heater samples of the fifth experimental example.

A temperature distribution along the longitudinal direction is examined in the samples of No. 21-a of the embodiment, and No. 26 of the comparative example. The temperature is measured along a longitudinal center line extending longitudinally through the center of the gas sensitive element 16 shown in FIG. 2 with the above-mentioned thermometer. FIG. 14 shows the results.

As known from FIG. 11, the ceramic heater sample of the embodiment (Lot Nos. 18-a~24-d) can withstand higher voltages without suffering cracks since the length C of the middle portion is smaller than the length A of the left and right lateral portions.

This withstanding ability against cracks is increased as the ratio C/A decreases. In particular, a desirable range for preventing cracks is $20 \leq C/S \leq 80$. More desirably, the ratio C/A is equal to or higher than 30 and equal to or smaller than 70 ($30 \leq C/S \leq 70$).

The samples identified by the suffix "c" and denoted by small triangles in FIG. 11, having an equal wire width between the middle and lateral regions and a wire spacing which is greater in the middle region than in the lateral regions are more resistant to cracks than the samples identified by the suffix "a" and denoted by small circles in FIG. 11, having wire width and spacing which are both equal between the middle and lateral regions. Still more resistant to cracks are the samples, identified by the suffix "b" and denoted by small squares, having a wire which is wider in the middle region than in the lateral regions and spaced equally between the middle and lateral regions. In the samples of the suffix "d" (inverted black small triangles) having wire width and spacing both made greater in the middle, cracks are less likely to occur specifically in the range of $20\% \leq C/A \leq 90\%$, and the effect in the range of $20 \leq C/A \leq 80$ is comparable to that in the range of $C/A \leq 60\%$ of the "c" type. Thus, the anti-crack ability is further improved in the "d" type samples. In the samples of the comparative example (Lot No. 26) having a C/A of 100%, by contrast, cracks are readily produced by lower voltages.

As shown in FIG. 12, the number of cycles at an average life failure rate of 50% is high, and accordingly the wire is difficult to break in the samples according to the third embodiment (Lot Nos. 18-a~24-d) in which the length C of the middle subsection is smaller than the length A of the lateral subsections. As the ratio C/A becomes lower, the possibility of breakage of a wire is decreased. In particular, a desirable range for preventing wire breaking is 20≦C/A≦80. A more desirable range to protect the ceramic heater against wire breaking is 30≦C/A<70. The possibility of wire breaking becomes lower in the order of the suffixes "a" (small circles) , "c" (small white triangles), "b" (small squares), and "d" (inverted black triangles). Among the four different designs "a", "b", "c" and "d", the design of the suffix "d" is first most effective against both crack and wire disconnection, and the "b" type is second most effective. The samples of the comparative example (Lot No. 26) having a C/A of 100% are undesirable in that the number of cycles at the average life failure rate of 50% is low and they are more susceptible to broken wire.

As shown in FIG. 13, the temperature distribution is uniform along the widthwise direction of the substrate in the ceramic heater samples of No. 21-c (denoted by white small circles) and No. 21-d (inverted black small triangles) having the middle subsection shorter than the left and right lateral subsections, as compared with the samples of the comparative example (No. 26, denoted by black small circles) in which C/A=100%. Thus, the heater pattern design according to the third embodiment can prevent cracks and breakage of wire more effectively by making the temperature distribution flatter.

As shown in FIG. 14, the temperature distribution along the longitudinal direction of the substrate is uniform in the ceramic heater samples of No. 21-a and No. 21-d having the middle subsection shorter than the left and right lateral subsections, as compared with the samples of the comparative example (No. 26) in which C/A=100%. The heater pattern design according to the third embodiment can prevent cracks and breakage of wire more effectively by making the slope of the longitudinal temperature distribution gentler. In the case of No. 21-d having the thicker wire segments spaced wider in the middle subsection, the temperature is slightly lowered near the center line. This design, therefore, can prevent cracks and wire breakage effectively by repressing thermal expansion around the center of the ceramic substrate.

Fourth Embodiment

Figure 15:
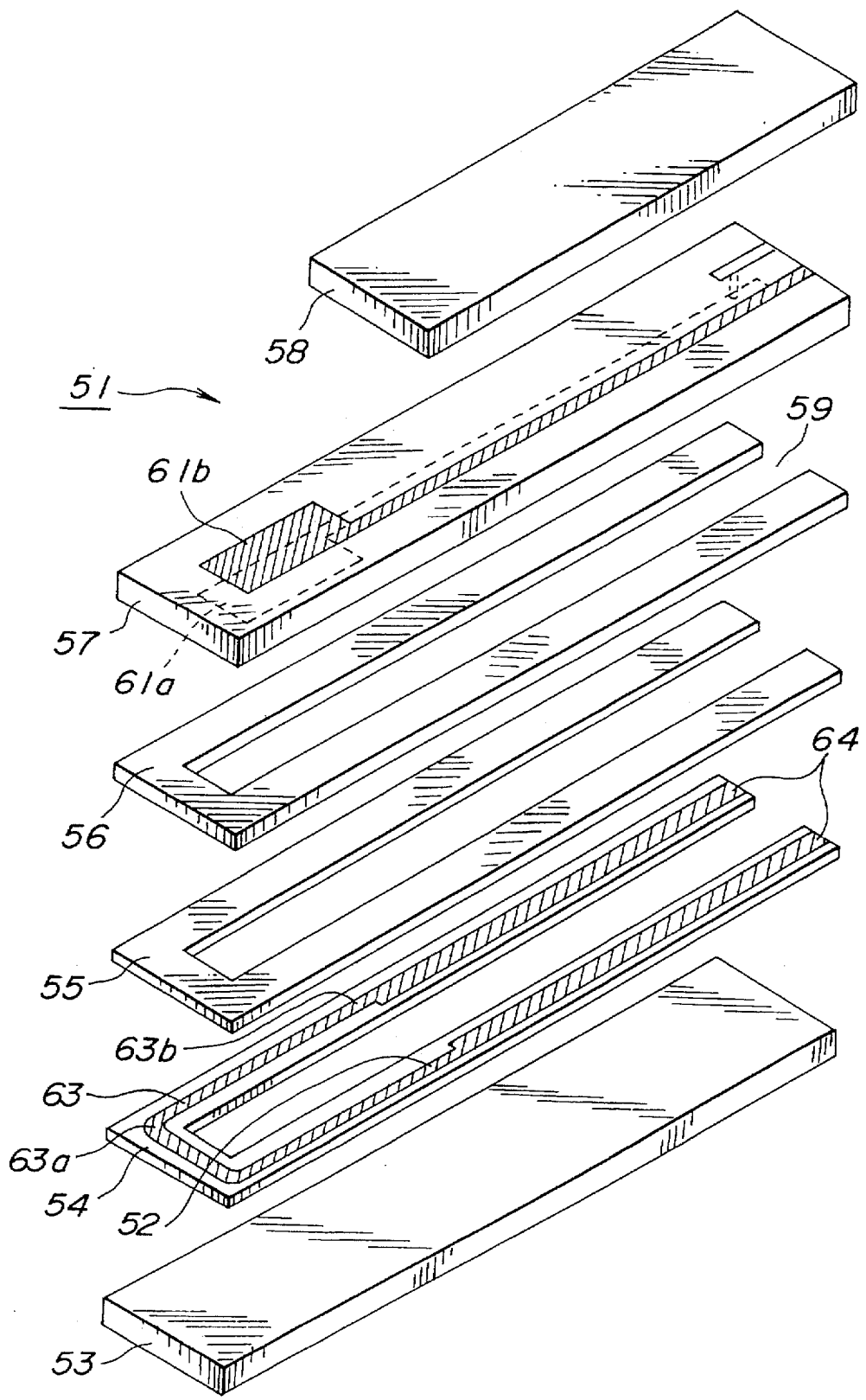
FIG. 15 is an exploded perspective view of an oxygen sensing device according to a fourth embodiment of the present invention.

FIG. 15 shows an example according to a fourth embodiment of the present invention. In this example, a ceramic heater is integrally formed in an oxygen sensing device having a sensitive element of zirconia.

An oxygen sensing device 51 shown in FIG. 15 is in the form of a substantially rectangular plate like the preceding examples, and has a width of 5 mm, a length of 45 mm, and a thickness of 2.4 mm. A heater pattern 52 is formed in this oxygen sensing device 51.

The oxygen sensing device 51 comprises a 0.8 mm thick zirconia•yttria substrate 53 shaped like a plate, a 0.2 mm thick first alumina U-shaped member 54, a 0.2 mm thick second alumina U-shaped member 55, a 0.4 mm thick U-shaped zirconia member 56, and a 0.8 mm thick zirconia substrate 57 shaped like a plate, which all constitute a laminated structure. This laminated structure further includes a short alumina reinforcing plate 58 provided on a base side portion of the zirconia substrate 57. The U-shaped plate-like members 54, 55 and 56 define an internal cavity 59 in which reference gas is introduced.

In this oxygen sensing device 51, there are formed, on the two opposite (upper and lower) surfaces of the zirconia substrate 57, a pair of porous electrodes 61a and 61b of platinum for detecting an electromotive force. The heater pattern 52 is placed between the first alumina member 54 and the second alumina member 55. The heater pattern 52 extends so as to describe a letter U along the U-shaped first alumina member 54. The heater pattern 52 has a U-shaped heating section 63 near the tip side end of the alumina plate 54, and a pair of leads 64 extending from the left and right ends of the heater section 63, respectively, to the base side end.

In this embodiment, the wire width of the heating section 63 is made greater in a tip side subsection 63a than in a base side subsection 63b, so that the resistance of the tip side subsection 63a is made lower than that of the base side subsection 63b. With this design, the heating section 63 produce less heat in the tip side subsection 63a than in the base side subregion 63b.

<Sixth Experimental Example>

A sixth experiment is to confirm effects of the oxygen sensing device having a heater pattern design according to the fourth embodiment.

Figure 16A:
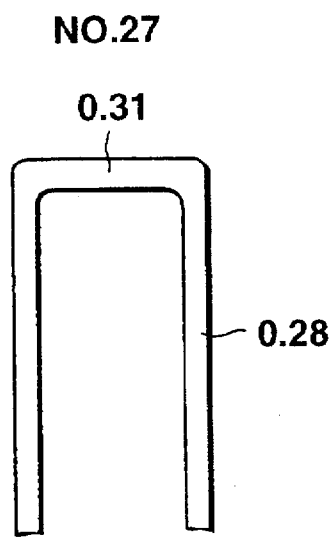
FIGS. 16A, 16B, 16C and 16D are schematic views for illustrating heater patterns used in a sixth experimental example for the fourth embodiment.
Figure 16B:
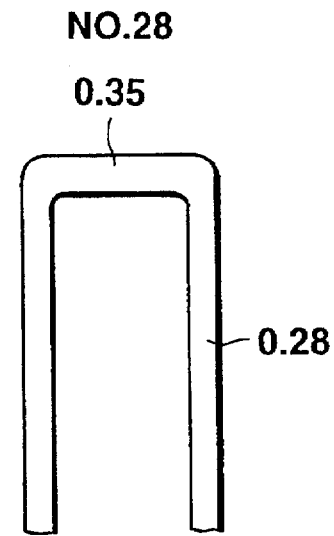
Figure 16C:
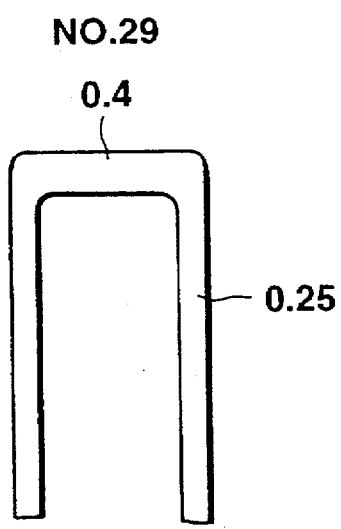
Figure 16D:
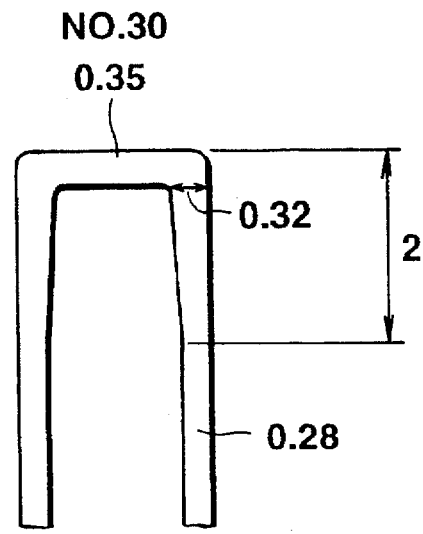

As shown in FIGS. 16A~16D, the total resistance of the heater pattern is about 10 Ω (the resistance of the heating section is 5.6 Ω), the length of the leads is 30 mm, the wire width of the leads is 0.8 mm, the longitudinal dimension of the heating section is 12 mm, and the lateral dimension of the heating section is 4.4 mm. The wire width of the base side subsection 63b of the heating section 63 is 0.28 mm. As listed in Table 6 of FIG. 17A, the wire width in the tip side region is different from that in the base side region in the samples of Lot Nos. 27~30 according to the fourth embodiment. In a comparative example of No. 31, the wire width is equal between the tip side subsection and the base side subsection. Each lot contains 25 samples. In the samples of Nos. 27~29, only a laterally extending subsection of the heating section is made greater in wire width. In the case of No. 30, the wire width is made greater in a tip side region which extends from the tip side end of the heating section longitudinally to a position at 2 mm apart from the tip side end, as shown in FIG. 16D. In this case, the tip side subsection having a greater wire width consists of a laterally extending subsection and left and right subsections extending longitudinally toward the base side from the left and right ends of the laterally extending subsection.

Figures 17, 17A:
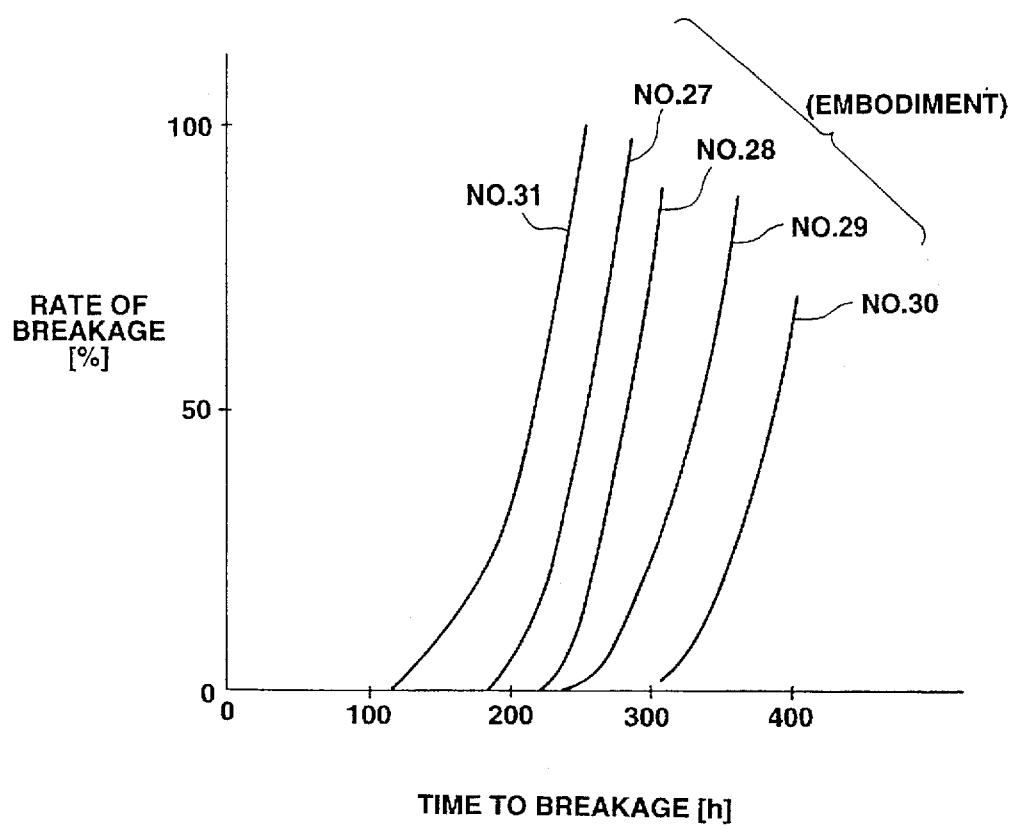
FIG. 17 is a graph showing the rate of wire breakage in the samples of the sixth experimental example.
FIG. 17A is a table showing features of the samples used in the sixth experimental example.
Figure 18A:
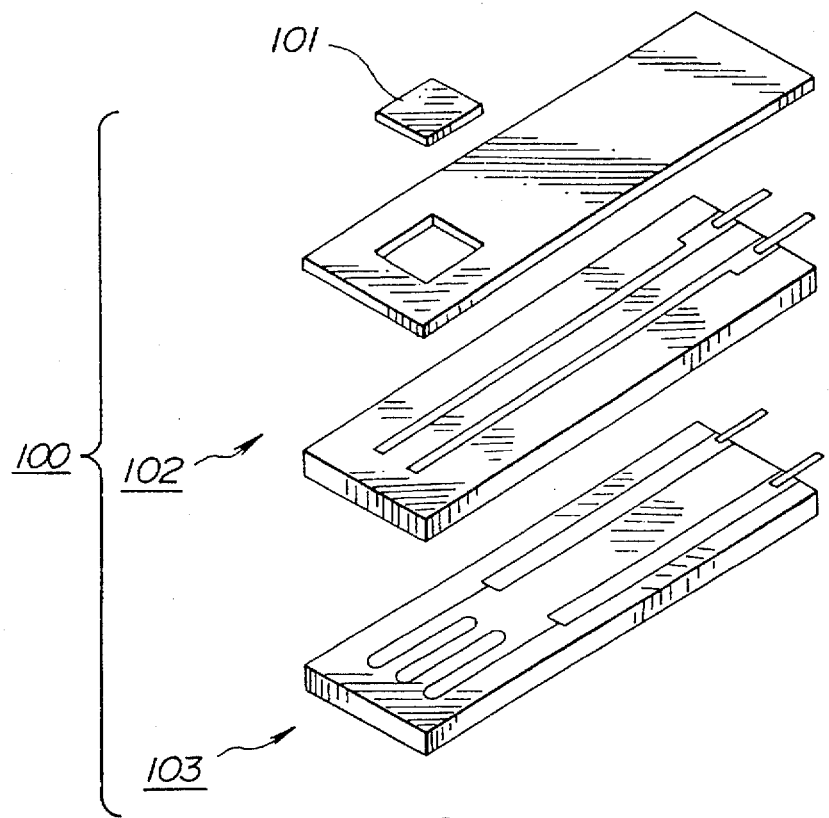
FIG. 18A is an exploded perspective view showing a conventional oxygen sensing device.
Figure 18B:
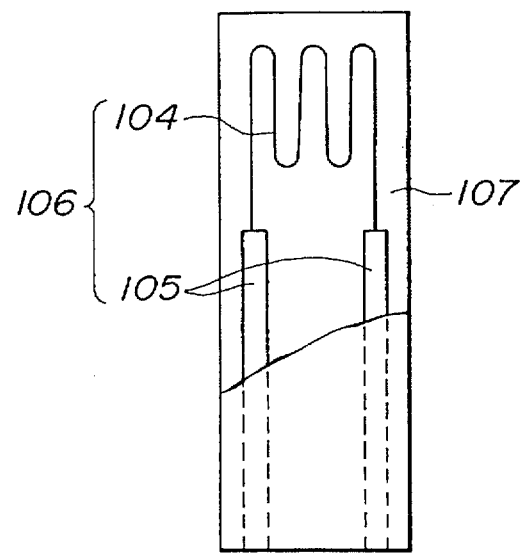
FIG. 18B is a plan view showing, partly in cutaway, a ceramic heater of the conventional example shown in FIG. 18A.

The heater pattern of each sample having a heater resistance (total resistance) of about 10 Ω is incorporated in an oxygen sensor by using a ceramic holder and glass seal in a known manner. Each oxygen sensor was placed in an electric furnace, the temperature of an ambient atmosphere (the atmosphere) was increased to 800 ° C., and a DC voltage of 18 V was applied. With these conditions, a time for a wire to reach a broken condition was measured. FIG. 17 shows the results.

As evident from FIG. 17, the samples according to the fourth embodiment can withstand application of higher voltages for a long time at a high temperature without failure of broken wire whereas the wire in the comparative example (No. 31) is readily broken.

As explained above, a device according to the illustrated embodiments of the present invention, having at least a function of heating, comprises: a first ceramic substrate extending longitudinally from a base side substrate end to a tip side substrate end; and a heating pattern which is formed on a first surface of said ceramic substrate, which extends from a first terminal to a second terminal, and which comprises a first lead extending from said first terminal toward said tip side substrate end and terminates at a first tip side lead end, a second lead extending from said second terminal toward said tip side substrate end and terminates at a second tip side lead end, and a heating element connecting said first and second tip side lead ends of said first and second leads and extends in a heating region (or heating zone) of said first surface of said ceramic substrate. The heating element is so formed as to generate less heat in a tip side subregion of said heating region than in a base side subregion of said heating region. The tip side subregion is located between said tip side substrate end of said ceramic substrate and said base side subregion, along the longitudinal direction of the substrate. In this device, the resistance per unit length of said heating element is lower in said tip side subregion than in said base side subregion.

According to one of possible interpretations, the first ceramic substrate corresponds to one of the alumina substrate 21 shown in FIG. 2, the alumina substrate 33 shown in FIG. 6, the alumina substrate 41 of FIG. 10 and the U-shaped alumina member 54 of FIG. 15.

The heating element may be printed on the substantially flat first surface of the first ceramic substrate so that the thickness of the heating element is much smaller than the wire width. For example, the wire thickness of the heating element is in the order of 20 mm.

The device according to the invention may further have a function of sensing oxygen. In this case, the heating and sensing device according to the present invention may further include a gas sensitive element (such as the item 16 or 34, for example) which is mounted on the second ceramic substrate 15 in the example of FIG. 2, or on the same first ceramic substrate 33 in the example of FIG. 6.

Alternatively, the heating and sensing device may further comprises first and second covering substrates (such as the zirconia yttria substrate 53, and the zirconia substrate 57, for example), a reference electrode (such as the electrode 61a, for example) formed on a first surface of said second covering substrate, and a sensing electrode (such as the electrode 61b, for example) formed on a second surface of said second covering substrate. In this case, the first ceramic substrate (such as the alumina substrate 54, for example) is U-shaped, and comprises a lateral section extending laterally between left and right ends, and left and right longitudinal sections extending, respectively, from said left and right ends of said lateral section longitudinally. The first ceramic substrate is tightly interposed between the first and second covering substrates so that a reference gas chamber is defined by said first ceramic substrate, said first covering substrate, and said first surface of said second covering substrate.

It is possible to form the heater pattern by a printing technique using an ink comprising conductive material such as Pt and W, ceramic (such as the same material of the ceramic substrate) and organic solvent. In the illustrate examples of the present invention, the conductive material of the ink is Pt (particle size is 0.5 μm), the ceramic of the ink is Al$_2$O$_3$ (particle size is 0.5 μm), and the wire thickness of the printed heater pattern (after firing) is 20 μm.

What is claimed is:

1. A ceramic heater for a sensor, comprising:
   a ceramic substrate extending in a longitudinal direction of the substrate from a base side substrate end to a tip side substrate end; and
   a heater pattern formed on said ceramic substrate, said heater pattern comprising a heating section for generating heat in a heating region near said tip side substrate end, and first and second lead sections extending from said heating section in the longitudinal direction of the substrate toward said base side substrate end, the first and second lead sections being spaced apart from each other in a direction perpendicular to the longitudinal direction, the heating section extending from the first lead section to the second lead section to form a current path;
   wherein said heating section comprises first and second base side subsections and a tip side subsection having first and second ends which are spaced apart from each other in the direction perpendicular to the longitudinal direction, said first base side subsection extending from said first end of said tip side subsection in the longitudinal direction to an end of said first base side subsection toward said base side substrate end, the second base side section extending from the second end of the tip side subsection to an end of said second base side subsection toward said base side substrate end, the first base side subsection, the tip side subsection and the second base side subsection being connected in series to form a series circuit between said ends of said first and second base side subsections, said tip side subsection further having a resistance per unit length lower than a resistance per unit length of said first base side subsection and lower than a resistance per unit length of said second base side subsection so that a less amount of heat is generated in said tip side subsection than in said first and second base side subsections.

2. A ceramic heater according to claim 1, wherein a wire width of said tip side subsection of said heating section is greater than a wire width of said first base side subsection, and greater than a wire width of said second base side subsection.

3. A ceramic heater according to claim 1, wherein a resistance of said tip side subsection of said heating section is smaller than a resistance of said first base side subsection, and smaller than a resistance of said second base side subsection.

4. A ceramic heater according to claim 1 wherein the first and second base side subsections of the heating section are located between the tip side subsection and a longitudinal middle of the ceramic substrate between the base side substrate end and the tip side substrate end.

5. A ceramic heater according to claim 4 wherein the first and second lead sections extend in the longitudinal direction of the ceramic substrate from the base side substrate end beyond the middle of the ceramic substrate toward the tip side substrate end, said heating section and said lead sections being in the form of a wire, and each lead section having a wire width greater than the wire width of the heating section.

6. A ceramic heater according to claim 5 wherein said heating pattern extends from a first terminal to a second terminal so as to form only a single current path extending from the first terminal to the second terminal, the first and second terminals both being located at the base side substrate end.

7. An oxygen sensor comprising:
   a sensing section comprising a gas sensitive element, and an output takeout section connected with said gas sensitive element;
   a heater arranged so as to surround said takeout section;
   a ceramic substrate supporting said sensing section and said heater; and
   a metal case fixedly supporting a base side portion of said ceramic substrate and enclosing said ceramic substrate;

wherein said heater comprises first and second lead sections, and a heating section which comprises first and second base side subsections and a tip side subsection having first and second ends, said first and second base side subsections extending, respectively, from said first and second ends of said tip side subsection toward said base side portion of said ceramic substrate, said first and second base side subsections being juxtaposed with each other, the first base side subsection extending in a longitudinal direction of the substrate from the first end of the tip side subsection to the first lead section and the second base side subsection extending in the longitudinal direction from the second end of the tip side subsection to the second lead section, the tip side subsection extending in a direction perpendicular to the longitudinal direction, said tip side subsection further having a resistance per unit length lower than a resistance per unit length of said first base side subsection and lower than a resistance per unit length of said second base side subsection so that a less amount of heat is generated in said tip side subsection than in said first and second base side subsection; and wherein the oxygen sensor further comprises a support member supporting the ceramic substrate only at the base side portion in the metal case, and the ceramic substrate projects in the metal case from the support member without being in contact with the support member at the tip side substrate end.

8. An oxygen sensor according to claim 7 wherein said gas sensitive element is made of a metal oxide whose resistance varies in dependence on an oxygen concentration, and said heater and said takeout section are formed substantially on an identical surface.

9. An oxygen sensor according to claim 7 wherein said gas sensitive element is made of a metal oxide whose electromotive force varies in accordance with an oxygen concentration, and said heater and said takeout section are formed on different surfaces.

10. An oxygen sensor according to claim 7 wherein the ceramic substrate extends in the longitudinal direction from a base side substrate end to a tip side substrate end, and wherein the first and second base side subsections of the heating section are located between the tip side subsection and a longitudinal middle of the ceramic substrate between the base side substrate end and the tip side substrate end, and wherein the heater extends from a first terminal to a second terminal so as to form only a single current path extending from the first terminal to the second terminal, the first and second terminals both being located at the base side substrate end.

11. An oxygen sensing device comprising:

an oxygen sensing means comprising an oxygen sensing portion;

a first ceramic substrate extending in a longitudinal direction from a base side substrate end to a tip side substrate end, said substrate being jointed with said oxygen sensing means; and a heating pattern which is formed on a first surface of said ceramic substrate, which forms a single current path by extending from a first terminal located at said base side substrate end to a second terminal located at said base side substrate end, and which comprises a first lead extending from said first terminal toward said tip side substrate end and terminates at a first tip side lead end, a second lead extending from said second terminal toward said tip side substrate end and terminates at a second tip side lead end, and a single heating wire for heating said oxygen sensing portion of said oxygen sensing means, said heating wire connecting said first and second tip side lead ends of said first and second leads, and the first lead, the wire and the second lead being connected in series so as to form a series circuit between the first and second terminals on the first surface of the ceramic substrate, so that a common current flows through all of the first and second leads and the single heating wire, the heating wire extending in a heating region of said first surface of said ceramic substrate, said heating region being located between said tip side substrate end of said first ceramic substrate and said first and second leads, said heating wire being so formed as to generate less heat in a tip side subregion in said heating region than in a base side subregion of said heating region, said tip side subregion being located between said tip side substrate end of said ceramic substrate and said base side subregion, wherein a resistance per unit length of said heating wire is lower in said tip side subregion than in said base side subregion;

wherein said heating wire is in a form of a single stripe-shaped wire, and a wire width of said heating wire is made greater in said tip side subregion than in said base side subregion;

wherein said heating wire comprises a U-shaped wire segment consisting of first and second longitudinal wire segments each extending from a base side segment end to a tip side segment end which is closer to said tip side substrate end than said base side segment end, and a tip side lateral wire segment extending in a widthwise direction perpendicular to said longitudinal direction of said first ceramic substrate, and connecting said tip side segment ends of said first and second longitudinal wire segments, the wire width of said tip side lateral wire segment of said heating wire is greater than the wire width of each of said first and second longitudinal wire segments at the base side segment end;

wherein the heating region is located between the tip side substrate end and a longitudinal middle of the substrate between the tip side substrate end and the base side substrate end; and wherein the oxygen sensing device further comprises a support member supporting the ceramic substrate, and the ceramic substrate projects from the support member and so as to be free from the support member at the tip side substrate end.

12. A device according to claim 11 wherein an electric resistance of said heating element is lower in said tip side subregion than in said base side subregion.

13. A device according to claim 11 wherein said heating element has a cross sectional area which is made greater in said tip side subregion than in said base side subregion.

14. A device according to claim 11 wherein a total length of said heating element in said tip side subregion of said heating region is smaller than a total length of said heating element in said base side subregion.

15. A device according to claim 11 wherein the wire width of said heating element becomes smaller as a monotone nonincreasing function of a distance from said tip side substrate end along the longitudinal direction of said substrate.

16. A device according to claim 11 wherein each of said first and second segments is tapered so that the wire width becomes smaller toward the base side segment end.

17. A device according to claim 11 wherein said tip side lateral segment is in a form of a curved line segment extending so as to make a U turn.

18. A device according to claim 11 wherein said heating element further comprises a base side lateral segment and another U-shaped segment consisting of third and fourth longitudinal segments each extending from a base side segment end to a tip side segment end longitudinally toward said tip side substrate end, and a tip side lateral segment extending semicircularly from said tip side segment end of said third longitudinal segment to said tip side segment end of said fourth longitudinal segment; said base side lateral segment extending semicircularly from said base side segment end of said third longitudinal segment to said base side segment end of said second longitudinal segment; and the wire width of each of said tip side lateral segments is greater than the wire width of said base side curved lateral.

19. A device according to claim 11 wherein said heating element meanders in said heating region and comprises a plurality of long longitudinal segments extending along the longitudinal direction of said ceramic substrate over both of said tip side subregion and said base side subregion, and short longitudinal segments extending along the longitudinal direction of said ceramic substrate only in said base side subregion.

20. A device according to claim 19 wherein said short longitudinal segments are situated between part of said long longitudinal segments and the remaining part of said long longitudinal segments; said long and short longitudinal segments are all straight and parallel to one another; and an interval between adjacent two of said short longitudinal segments is greater than an interval between adjacent two of said long longitudinal segments.

21. A device according to claim 11, further comprising a second ceramic substrate and a gas sensitive element mounted on said second ceramic substrate; and said heater pattern is interposed between said first and second ceramic substrate.

22. A device according to claim 11, further comprising a gas sensitive element mounted on said first surface of said first ceramic surface, and a pair of electrodes formed on said first surface of said first ceramic substrate; and said heater pattern extends in said first surface of said first ceramic substrate so as to surround said sensing element and said electrodes.

23. A device according to claim 11, further comprising first and second covering substrates, a reference electrode formed on a first surface of said second covering substrate, and a sensing electrode formed on said second surface of said second covering substrate; said first ceramic substrate is U-shaped, and comprises a lateral section extending laterally between left and right ends, and left and right longitudinal sections extending longitudinally, respectively, from said left and right ends of said lateral section; said first ceramic substrate is tightly interposed between said first and second covering substrates so that a reference gas chamber is defined by said first ceramic substrate, said first covering substrate, and said first surface of said second covering substrate; and said second covering substrate is made of metal oxide.

24. A device comprising:
a ceramic substrate extending longitudinally from a base side substrate end to a tip side substrate end; and
a heating pattern which is formed on a first surface of said ceramic substrate, which extends from a first terminal to a second terminal, and which comprises a first lead extending from said first terminal toward said tip side substrate end and terminates at a first tip side lead end, a second lead extending from said second terminal toward said tip side substrate end and terminates at a second tip side lead end, and a heating element connecting said first and second tip side lead ends of said first and second leads and extending in a heating region of said first surface of said ceramic substrate, said heating element being so formed as to generate less heat in a tip side subregion in said heating region than in a base side subregion of said heating region, and to generate less heat in a middle subregion in said heating region than in first and second lateral side subregions, said tip side subregion being located longitudinally between said tip side substrate end of said ceramic substrate and said base side subregion, and said middle subregion being located laterally between said first and second lateral side subregions.

25. A device according to claim 24 wherein said heating element is in a form of a stripe-shaped wire, and comprises a plurality of longitudinal segments extending substantially in parallel to each other along a longitudinal direction of said first ceramic substrate, and wherein one of a wire width of said heating element and a wire spacing between two adjacent longitudinal segments of said heating element is made greater in said tip side subregion than in said base side subregion, and one of the wire width and the wire spacing of said heating element is made greater in said middle subregion than in said first and second lateral side subregions.

26. A ceramic heater for a sensor, comprising:
a ceramic substrate; and
a heater pattern formed on said ceramic substrate, said heater pattern comprising a heating section for generating heat, and a lead section extending from said heating section;
wherein said heating section of said heater pattern comprises a meandering portion which comprises first and second lateral side portions and a middle portion which is located between said first and second lateral side portions, which is shorter along a longitudinal direction of said ceramic substrate than said lateral side portions, and which is situated toward the base side, and an amount of heat per unit area of said substrate, produced by said heater pattern is smaller in said middle portion than in said first and second lateral side portions.

27. A ceramic heater according to claim 26 wherein a length of said middle portion of said heating section along said longitudinal direction is equal to or smaller than 70% of a length of said lateral portions along said longitudinal direction.

28. A ceramic heater according to claim 26 wherein a wire width of said middle portion of said heating section is larger than a wire width of said lateral side portions.

29. A ceramic heater according to claim 26 wherein a wire spacing in said middle portion of said heating section is greater than a wire spacing in said lateral portions.

30. A ceramic heater according to claim 26 wherein said heating section has a resistivity S in a tip side region and a resistivity T in a base side region, and a ratio T/S is equal to or greater than 1.22.

* * * * *